US006337192B1

(12) United States Patent
Bartel et al.

(10) Patent No.: US 6,337,192 B1
(45) Date of Patent: Jan. 8, 2002

(54) MMSC1-AN MMAC1 INTERACTING PROTEIN

(75) Inventors: Paul L. Bartel; Sean V. Tavtigian, both of Salt Lake City, UT (US)

(73) Assignee: Myraid Genetics, Inc., Salt Lake City, UT (US)

( * ) Notice: Subject to any disclaimer, the term of this patent is extended or adjusted under 35 U.S.C. 154(b) by 0 days.

(21) Appl. No.: 09/233,086

(22) Filed: Jan. 19, 1999

Related U.S. Application Data

(60) Provisional application No. 60/071,861, filed on Jan. 20, 1998.

(51) Int. Cl.[7] .......................... C12N 15/00; C12N 5/00; C12N 15/63; C07H 21/02; C07H 12/04
(52) U.S. Cl. ................... 435/69.1; 435/325; 435/320.1; 536/23.1
(58) Field of Search ............................... 536/23.1, 24.3; 435/320.1, 325, 70.1, 69.1

(56) References Cited

FOREIGN PATENT DOCUMENTS

| | | |
|---|---|---|
| WO | 8804178 | 6/1988 |
| WO | 9506735 | 3/1995 |

OTHER PUBLICATIONS

J. Rudinger, Biological Council, Peptide Hormones, "Characteristics of the amino acids as components of a peptide hormone sequence," (University Park Press), Jun. 1976, pp. 1–7.*
Homo sapiens, Accession No. AJ224747, 1997.*
Homo sapiens, Accession No. H51684, 1995.*
Homo sapiens, Accession No. R98435, 1995.*
W. French Anderson, Huwan gene therapy, Nature, vol. 3925, pp. 25–30, 1998.*
Brakeman, et al., "Homer: a protein that selectively binds metabotropic glutamate receptors", Nature, vol. 386, pp. 284–288, Mar. 20, 1997.
Brenman, et al., "Interaction of Nitric Oxide Synthase with the Postsynaptic Density Protein PSD–95 and α1–Synthrophin Mediated by PDZ Domains", Cell, vol. 84, pp. 757–767, Mar. 8, 1996.
Chevesich, et al, "Requirement for the PDZ Domain Protein, INAD, for Localization of the TRP Store–Operated Channel to a Signaling Complex", Neuron, vol. 18, pp. 95–105, Jan. 1997.
Dong, et al., "GRIP: a synaptic PDZ domain–containing protein that interacts with AMPA receptors", Nature: vol. 386, pp. 279–284, Mar. 20, 1997.

Doyle, et al., Crystal Structures of a Complexed and Peptide–Free Membrane Protein–Binding Domain: Molecular Basis of Peptide Recognition by PDZ, Cell, vol. 85, pp. 1067–1076, Jun. 28, 1996.
Furnari, et al., "Growth suppression of glioma cells by PTEN requires a functional phosphatase catalytic domain", Proc. Natl.Acad.Sci., vol. 94, pp. 12479–12484, Nov. 1997, Genetics.
Irie,et al., "Binding of Neuroligins to PSD–95", Science, vol. 277, pp. 1511–1515, Sep. 5, 1997.
Kim, et al., "Clustering of Shaker–type K+ channel by interaction with a family of membraine–associated guanylate kinases", Nature, vol. 378, pp. 85–88, Nov. 2, 1995.
Kornau, et al., "Domain Interaction Between NMDA Receptor Subunits and the Postsynaptic Density Protein PSD–95", Science, vol. 269, pp. 1737–1740, Sep. 22, 1995.
Li et al., PTEN, a Putative Protein Tyrosine Phosphatase Gene Mutated in Human Brain, Breast and Prostate Cancer, Science, vol. 275, pp. 1943–1747, Mar. 28, 1997.
Pawson, et al., "Signaling Through Scaffold, Anchoring and Adaptor Proteins", Science, vol. 278, pp. 2075–2080, Dec. 19, 1997.
Philipp, et al.(1997), "Molecular characterization of a novel human PDZ domain protein with homology to INAD from *Drosophila melanogaster*", FEBS Lett.413, No. 2, pp. 243–248; Jun. 6, 1997.
Shieh, et al., "Regulation of TRP $Ca^{2+}$ Channel by INAD in Drosophila Photoreceptors", Neuron, vol. 16, pp. 991–998, May 1996.
Simske, et al., "LET–23 Receptor Localization by the Cell Junction Protein LIN–7 during C. elegans Vulval Induction", pp. 195–204, Apr. 19, 1996., CELL
Songyang, et al., "Recognition of Unique Carboxyl–Terminal Motifs by Distinct PDZ Domains", Science, vol. 275, pp. 73–77, Jan. 3, 1997.
Steck, et al., Identification of a candidate tumour suppressor gene, MMAC1, at chromosome 10q23.3 that is mutated in multiple advanced cancers, Nature Genetics, vol. 15, pp. 356–362, Apr. 1997.
Tsunoda, et al., "A multivalent PDZ–domain protein assemblies signalling complexes in a G–protein–coupled cascade", Nature, vol. 388, pp. 243–249, Jul. 17, 1997.

* cited by examiner

Primary Examiner—Dave T. Nguyen
Assistant Examiner—Ram R. Shukla
(74) Attorney, Agent, or Firm—Rothwell, Figg, Ernst & Manbeck

(57) ABSTRACT

The present invention is directed to the MMSC1 gene, its protein product and the use of the protein to (i) detect mutant MMAC1 proteins, (ii) screen for drugs which can be used for suppressing tumor growth and (iii) identify proteins which interact with the MMAC1 gene or are involved in the tumor suppression pathway of the MMAC1 gene.

16 Claims, 2 Drawing Sheets

```
H.s._MMSC1      0  CTCACTTCCGCCCAGGTGAGGCAGGCCGACACCGAGCCCGCCGACCCGGCTCCCACC
M.m._MMSC1      0  ACTTCCGCC-AGTGAGG-AGG-CCG- TCCGTGCCGCCCCAGCCCCCGGGGCTCCCACC
                   -----|-----|-----|-----|-----|-----|-----|-----|-----|-----|
                        11    21    31    41    51

H.s._MMSC1     60  TGCTCCTCCAGCGCACCAGGTGTCTTTAAGAGTGATTGAAGAGAATAATTCAAAATGCCT
H.s._MMSC1.pep  0                                                            M--P--
M.m._MMSC1     52  CCGCCGTCGCCCGATCAGAC--TTTTTGGAAGTGATTGAAAAGAATATCCCAAAATGCCT
M.m._MMSC1.pep  0                                                            M--P--
                   -----|-----|-----|-----|-----|-----|-----|-----|-----|-----|
                        71    81    91   101   111

H.s._MMSC1    120  GAAAATCCTGCTACAGATAAACTGCAGGTGCTGCAGGTACTTGATCGCCTGAAATGAAA
H.s._MMSC1.pep  2  E--N--P--A--T--D--K--L--Q--V--L--Q--V--L--D--R--L--K--M--K--
M.m._MMSC1    110  GAAAACCCTGCTGCAGAAGATGCAGGTCCTGCAGGTCCTGGATCGCCTTCGAGGGAAG
M.m._MMSC1.pep  2  E--N--P--A--A--E--K--M--Q--V--L--Q--V--L--D--R--L--R--G--K--
                   -----|-----|-----|-----|-----|-----|-----|-----|-----|-----|
                       131   141   151   161   171

H.s._MMSC1    180  TTGCAGGAGAAGGGTGACACGTCGCAGAATGAGAAGTTATCTATGTTTTATGAGACACTA
H.s._MMSC1.pep 22  L--Q--E--K--G--D--T--S--Q--N--E--K--L--S--M--F--Y--E--T--L--
M.m._MMSC1    170  CTGCAGGAGAAGGGAGAGGGAGACACGCCAGAACGCAGAAGCTGTCTGCTTCTACGAGACGCTG
M.m._MMSC1.pep 22  L--Q--E--K--G--D--T--Q--N--E--K--L--S--A--F--Y--E--T--L--
                   -----|-----|-----|-----|-----|-----|-----|-----|-----|-----|
                       191   201   211   221   231

H.s._MMSC1    240  AAGAGTCCTCTCTTCAACCAGATACTCACACTTCAGCAGTCCATCAAGCAACTGAAGGGT
H.s._MMSC1.pep 42  K--S--P--L--F--N--Q--I--L--T--L--Q--Q--S--I--K--Q--L--K--G
M.m._MMSC1    230  AAGAGCCCTCTCTTCAACCAGATCCTTACACTGCAGCAGTCCATCAAGCAGCTGAAGGGA
M.m._MMSC1.pep 42  K--S--P--L--F--N--Q--I--L--T--L--Q--Q--S--I--K--Q--L--K--G
                   -----|-----|-----|-----|-----|-----|-----|-----|-----|-----|
                       251   261   271   281   291
```

FIG. 2

SEQUENCE LISTING

<160> NUMBER OF SEQ ID NOS: 65

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:PDZ
      Consensus Domain
<220> FEATURE:
<221> NAME/KEY: PEPTIDE
<222> LOCATION: (2)..(4)
<223> OTHER INFORMATION: Xaa at residue 2 may be Ser or Thr; Xaa at
      residue 3 may be any amino acid; Xaa at residue 4 may be
      Val or Ile.

<400> SEQUENCE: 1

Glu Xaa Xaa Xaa
 1

<210> SEQ ID NO 2
<211> LENGTH: 5836
<212> TYPE: DNA
<213> ORGANISM: Homo sapiens
<220> FEATURE:
<221> NAME/KEY: CDS
<222> LOCATION: (115)..(5757)

<400> SEQUENCE: 2

```
ctcacttccg cccaggtgag gcagggccga caccgagccc gcccgacccg ggctcccacc         60
tgctcctcca gcgcaccagg tgtctttaag agtgattgaa gagaataatt caaa atg        117
                                                            Met
                                                              1 cct gaa aat cct gct aca gat aaa ctg cag gtg ctg cag gta ctt gat        165
Pro Glu Asn Pro Ala Thr Asp Lys Leu Gln Val Leu Gln Val Leu Asp
         5                  10                  15 cgc ctg aaa atg aaa ttg cag gag aag ggt gac acg tcg cag aat gag        213
Arg Leu Lys Met Lys Leu Gln Glu Lys Gly Asp Thr Ser Gln Asn Glu
     20                  25                  30 aag tta tct atg ttt tat gag aca cta aag agt cct ctc ttc aac cag        261
Lys Leu Ser Met Phe Tyr Glu Thr Leu Lys Ser Pro Leu Phe Asn Gln
 35                  40                  45 ata ctc aca ctt cag cag tcc atc aag caa ctg aag ggt caa ctc aac        309
Ile Leu Thr Leu Gln Gln Ser Ile Lys Gln Leu Lys Gly Gln Leu Asn
 50                  55                  60                  65 cat ata ccc tca gat tgt tca gcc aac ttt gat ttt tct agg aaa ggt        357
His Ile Pro Ser Asp Cys Ser Ala Asn Phe Asp Phe Ser Arg Lys Gly
                 70                  75                  80 ttg tta gtg ttc aca gat ggt tcc att act aat gga aat gtc cac agg        405
Leu Leu Val Phe Thr Asp Gly Ser Ile Thr Asn Gly Asn Val His Arg
             85                  90                  95 ccc tct aat aac tcg act gta tct ggg tta ttt ccg tgg acc ccg aag        453
Pro Ser Asn Asn Ser Thr Val Ser Gly Leu Phe Pro Trp Thr Pro Lys
        100                 105                 110 ttg gga aat gaa gac ttt aac tca gtc att caa cag atg gct cag ggc        501
Leu Gly Asn Glu Asp Phe Asn Ser Val Ile Gln Gln Met Ala Gln Gly
    115                 120                 125 cgg caa att gaa tat ata gat ata gaa cgg cct tca act gga ggc ctt        549
Arg Gln Ile Glu Tyr Ile Asp Ile Glu Arg Pro Ser Thr Gly Gly Leu
130                 135                 140                 145 gga ttc agt gtg gtg gcc ctc aga agt caa aat ctc gga aaa gtt gat        597
Gly Phe Ser Val Val Ala Leu Arg Ser Gln Asn Leu Gly Lys Val Asp
                150                 155                 160 atc ttc gtg aag gat gtc cag cca ggg agt gta gca gac agg gat caa        645
Ile Phe Val Lys Asp Val Gln Pro Gly Ser Val Ala Asp Arg Asp Gln
            165                 170                 175 aga tta aag gaa aat gat caa ata ttg gcc att aat cac acg cca ttg        693
Arg Leu Lys Glu Asn Asp Gln Ile Leu Ala Ile Asn His Thr Pro Leu
        180                 185                 190 gat cag aac att tcc cat cag caa gca att gca tta tta caa caa acc        741
Asp Gln Asn Ile Ser His Gln Gln Ala Ile Ala Leu Leu Gln Gln Thr
    195                 200                 205 act gga tct ttg aga ctg att gtg gcc agg gaa cca gtc cac aca aaa        789
Thr Gly Ser Leu Arg Leu Ile Val Ala Arg Glu Pro Val His Thr Lys
210                 215                 220                 225 agc agt act tct agc agc cta aat gat aca act ctg cct gaa aca gtt        837
```

```
Ser Ser Thr Ser Ser Ser Leu Asn Asp Thr Thr Leu Pro Glu Thr Val
            230                 235                 240 tgt tgg ggc cat gtt gaa gag gtt gag ctc att aat gat ggc tct gga         885
Cys Trp Gly His Val Glu Glu Val Glu Leu Ile Asn Asp Gly Ser Gly
            245                 250                 255 cta ggt ttt gga ata gtt gga gga aaa aca agt ggc gtg gtt gtg agg         933
Leu Gly Phe Gly Ile Val Gly Gly Lys Thr Ser Gly Val Val Val Arg
            260                 265                 270 act ata gtt cct gga gga tta gca gat cga gat gga aga ctc cag aca         981
Thr Ile Val Pro Gly Gly Leu Ala Asp Arg Asp Gly Arg Leu Gln Thr
        275                 280                 285 ggg gac cac atc ttg aag att ggt ggc aca aac gtg cag gga atg acc        1029
Gly Asp His Ile Leu Lys Ile Gly Gly Thr Asn Val Gln Gly Met Thr
290                 295                 300                 305 agt gag caa gtt gca caa gtt cta agg aac tgt ggg aat tca gtc agg        1077
Ser Glu Gln Val Ala Gln Val Leu Arg Asn Cys Gly Asn Ser Val Arg
                310                 315                 320 atg ctc gtt gct aga gat cca gct ggt gac att tca gtc acc ccc cct        1125
Met Leu Val Ala Arg Asp Pro Ala Gly Asp Ile Ser Val Thr Pro Pro
            325                 330                 335 gcc cct gca gcc tta cct gtt gcc ctg cct act gta gcc agc aag ggc        1173
Ala Pro Ala Ala Leu Pro Val Ala Leu Pro Thr Val Ala Ser Lys Gly
            340                 345                 350 cct ggt tct gac agt tct ctt ttt gaa act tat aat gtt gag ctt gtg        1221
Pro Gly Ser Asp Ser Ser Leu Phe Glu Thr Tyr Asn Val Glu Leu Val
355                 360                 365 aga aaa gat ggg cag agt ctt gga att aga att gtt ggc tat gtt gga        1269
Arg Lys Asp Gly Gln Ser Leu Gly Ile Arg Ile Val Gly Tyr Val Gly
370                 375                 380                 385 aca tct cat aca ggg gaa gct tca ggg att tat gtg aaa agt gta ata        1317
Thr Ser His Thr Gly Glu Ala Ser Gly Ile Tyr Val Lys Ser Val Ile
                390                 395                 400 cct ggc agt gct gcg tac cac aat ggc cac att caa gtg aat gac aaa        1365
Pro Gly Ser Ala Ala Tyr His Asn Gly His Ile Gln Val Asn Asp Lys
            405                 410                 415 ata gtt gct gtc gat ggc gtg aac att cag ggt ttt gcc aac cat gat        1413
Ile Val Ala Val Asp Gly Val Asn Ile Gln Gly Phe Ala Asn His Asp
            420                 425                 430 gtt gtt gaa gta tta cga aat gca ggg cag gtg gta cac cta acc cta        1461
Val Val Glu Val Leu Arg Asn Ala Gly Gln Val Val His Leu Thr Leu
435                 440                 445 gtt cga agg aag aca tcc tca tct act tct cca ctt gaa cca cct tca        1509
Val Arg Arg Lys Thr Ser Ser Ser Thr Ser Pro Leu Glu Pro Pro Ser
450                 455                 460                 465 gac aga gga act gtt gta gaa cca ctg aaa cca cca gct ctc ttt cta        1557
Asp Arg Gly Thr Val Val Glu Pro Leu Lys Pro Pro Ala Leu Phe Leu
                470                 475                 480 act gga gca gtg gaa act gaa act aat gtg gat ggt gaa gat gag gaa        1605
Thr Gly Ala Val Glu Thr Glu Thr Asn Val Asp Gly Glu Asp Glu Glu
            485                 490                 495 att aaa gaa aga att gat act tta aaa aat gac aac ata caa gcc tta        1653
Ile Lys Glu Arg Ile Asp Thr Leu Lys Asn Asp Asn Ile Gln Ala Leu
            500                 505                 510 gaa aaa ttg gaa aaa gtc cca gac tct cca gaa aat gag ctg aaa tcc        1701
Glu Lys Leu Glu Lys Val Pro Asp Ser Pro Glu Asn Glu Leu Lys Ser
        515                 520                 525 aga tgg gaa aac ctg ttg ggt cct gat tat gaa gta atg gtt gct act        1749
Arg Trp Glu Asn Leu Leu Gly Pro Asp Tyr Glu Val Met Val Ala Thr
530                 535                 540                 545
```

| | |
|---|---|
| ttg gac aca cag att gca gat gat gct gag tta cag aaa tat tca aag<br>Leu Asp Thr Gln Ile Ala Asp Asp Ala Glu Leu Gln Lys Tyr Ser Lys<br>          550               555               560 | 1797 |
| ctg ctg cct att cac act ctg agg ctt ggt gtg gaa gtg gat tcc ttt<br>Leu Leu Pro Ile His Thr Leu Arg Leu Gly Val Glu Val Asp Ser Phe<br>     565               570               575 | 1845 |
| gat ggg cac cat tat att tct tca att gtt tct ggt ggt cct gtt gat<br>Asp Gly His His Tyr Ile Ser Ser Ile Val Ser Gly Gly Pro Val Asp<br>          580               585               590 | 1893 |
| aca ttg ggt ctc cta cag cca gaa gat gag ctg ctt gag gtc aat ggc<br>Thr Leu Gly Leu Leu Gln Pro Glu Asp Glu Leu Leu Glu Val Asn Gly<br>     595               600               605 | 1941 |
| atg cag ctt tat gga aaa tct cgc cga gaa gca gtc tcc ttt ctt aaa<br>Met Gln Leu Tyr Gly Lys Ser Arg Arg Glu Ala Val Ser Phe Leu Lys<br>610               615               620               625 | 1989 |
| gaa gtg cca ccc cct ttt act ttg gtt tgc tgt cgg agg ttg ttt gat<br>Glu Val Pro Pro Pro Phe Thr Leu Val Cys Cys Arg Arg Leu Phe Asp<br>               630               635               640 | 2037 |
| gat gaa gct tct gta gat gaa cca agg cgc act gaa acc tct ctt cct<br>Asp Glu Ala Ser Val Asp Glu Pro Arg Arg Thr Glu Thr Ser Leu Pro<br>               645               650               655 | 2085 |
| gag aca gag gtt gac cac aat atg gat gtc aat act gaa gaa gat gat<br>Glu Thr Glu Val Asp His Asn Met Asp Val Asn Thr Glu Glu Asp Asp<br>          660               665               670 | 2133 |
| gat ggg gaa tta gca ctg tgg tcc cct gaa gtc aag att gtt gaa cta<br>Asp Gly Glu Leu Ala Leu Trp Ser Pro Glu Val Lys Ile Val Glu Leu<br>675               680               685 | 2181 |
| gta aaa gat tgt aaa ggt ttg gga ttc agc att ttg gat tac cag gac<br>Val Lys Asp Cys Lys Gly Leu Gly Phe Ser Ile Leu Asp Tyr Gln Asp<br>690               695               700               705 | 2229 |
| cct tta gat cct aca aga tca gtg att gtg atc cgc tcc ctg gta gca<br>Pro Leu Asp Pro Thr Arg Ser Val Ile Val Ile Arg Ser Leu Val Ala<br>               710               715               720 | 2277 |
| gat ggt gta gca gaa aga agt ggg gga cta tta cct gga gac cgc ctg<br>Asp Gly Val Ala Glu Arg Ser Gly Gly Leu Leu Pro Gly Asp Arg Leu<br>          725               730               735 | 2325 |
| gtc tca gtc aat gaa tac tgt ttg gac aac acc tca ctt gct gaa gct<br>Val Ser Val Asn Glu Tyr Cys Leu Asp Asn Thr Ser Leu Ala Glu Ala<br>          740               745               750 | 2373 |
| gtg gaa ata ttg aaa gct gtg cca cca ggc cta gta cac ctt ggc atc<br>Val Glu Ile Leu Lys Ala Val Pro Pro Gly Leu Val His Leu Gly Ile<br>     755               760               765 | 2421 |
| tgt aag cct ttg gtg gaa gat aat gaa gaa gaa agt tgt tat att tta<br>Cys Lys Pro Leu Val Glu Asp Asn Glu Glu Glu Ser Cys Tyr Ile Leu<br>770               775               780               785 | 2469 |
| cat tca agc agt aat gaa gac aag act gaa ttt tca gga aca att cat<br>His Ser Ser Ser Asn Glu Asp Lys Thr Glu Phe Ser Gly Thr Ile His<br>               790               795               800 | 2517 |
| gat ata aat tca tct tta ata ctc gaa gca ccc aag gga ttt aga gat<br>Asp Ile Asn Ser Ser Leu Ile Leu Glu Ala Pro Lys Gly Phe Arg Asp<br>          805               810               815 | 2565 |
| gaa cca tat ttt aaa gaa gaa ctt gtg gat gaa cca ttt cta gat ctg<br>Glu Pro Tyr Phe Lys Glu Glu Leu Val Asp Glu Pro Phe Leu Asp Leu<br>          820               825               830 | 2613 |
| gga aag tct ttc cat tcc caa caa aaa gag ata gag caa agc aag gag<br>Gly Lys Ser Phe His Ser Gln Gln Lys Glu Ile Glu Gln Ser Lys Glu<br>835               840               845 | 2661 |
| gcc tgg gag atg cat gaa ttt ctg act cct aga ttg cag gaa atg gat<br>Ala Trp Glu Met His Glu Phe Leu Thr Pro Arg Leu Gln Glu Met Asp<br>850               855               860               865 | 2709 |

-continued

```
gaa gaa aga gaa atg ctt gtt gat gaa gaa tat gag tta tat caa gat    2757
Glu Glu Arg Glu Met Leu Val Asp Glu Glu Tyr Glu Leu Tyr Gln Asp
            870                 875                 880 ccc tca cca tcc atg gag ttg tat ccc ttg tcg cac att caa gag gcc    2805
Pro Ser Pro Ser Met Glu Leu Tyr Pro Leu Ser His Ile Gln Glu Ala
        885                 890                 895 act cct gtg ccc tct gtg aat gaa ctt cac ttt ggt aca cag tgg ttg    2853
Thr Pro Val Pro Ser Val Asn Glu Leu His Phe Gly Thr Gln Trp Leu
    900                 905                 910 cat gat aat gaa cca tcc gag tct caa gag gca aga acc ggg agg act    2901
His Asp Asn Glu Pro Ser Glu Ser Gln Glu Ala Arg Thr Gly Arg Thr
915                 920                 925 gtc tat tcc cag gag gca cag ccg tat ggc tat tgc cct gaa aat gtg    2949
Val Tyr Ser Gln Glu Ala Gln Pro Tyr Gly Tyr Cys Pro Glu Asn Val
930                 935                 940                 945 atg aaa gaa aat ttt gtc atg gag tcc cta cca tct gta cca tca act    2997
Met Lys Glu Asn Phe Val Met Glu Ser Leu Pro Ser Val Pro Ser Thr
            950                 955                 960 gaa gga aac agt caa caa ggc aga ttt gac gac ctg gaa aat ctt aat    3045
Glu Gly Asn Ser Gln Gln Gly Arg Phe Asp Asp Leu Glu Asn Leu Asn
        965                 970                 975 tca tta gca aaa act agt ctg gat tta ggc atg atc ccg aat gat gtc    3093
Ser Leu Ala Lys Thr Ser Leu Asp Leu Gly Met Ile Pro Asn Asp Val
    980                 985                 990 caa ggt cct agc ttg ctc att gac ctt cct gtt gtg gct caa agg agg    3141
Gln Gly Pro Ser Leu Leu Ile Asp Leu Pro Val Val Ala Gln Arg Arg
995                 1000                1005 gag caa gaa gat ttg cct tta tat caa cac caa gcg aca cga gtt att    3189
Glu Gln Glu Asp Leu Pro Leu Tyr Gln His Gln Ala Thr Arg Val Ile
1010                1015                1020                1025 tcc aag gcc tca gca tac aca gga atg ttg tct tct aga tat gcc act    3237
Ser Lys Ala Ser Ala Tyr Thr Gly Met Leu Ser Ser Arg Tyr Ala Thr
            1030                1035                1040 gat aca tgt gag tta cct gag aga gaa gaa ggc gaa gga gaa gaa act    3285
Asp Thr Cys Glu Leu Pro Glu Arg Glu Glu Gly Glu Gly Glu Glu Thr
        1045                1050                1055 cca aat ttt agc cac tgg ggt cca ccg aga att gtt gag att ttt aga    3333
Pro Asn Phe Ser His Trp Gly Pro Pro Arg Ile Val Glu Ile Phe Arg
    1060                1065                1070 gaa ccc aat gtg tct ctt ggg atc agt att gtt ggt gga caa act gtt    3381
Glu Pro Asn Val Ser Leu Gly Ile Ser Ile Val Gly Gly Gln Thr Val
1075                1080                1085 ata aaa cgt cta aag aat gga gag gag ctt aaa ggt ata ttc atc aaa    3429
Ile Lys Arg Leu Lys Asn Gly Glu Glu Leu Lys Gly Ile Phe Ile Lys
1090                1095                1100                1105 caa gtt tta gaa gac agt cca gca ggg aag acg aac gca ctt aaa act    3477
Gln Val Leu Glu Asp Ser Pro Ala Gly Lys Thr Asn Ala Leu Lys Thr
            1110                1115                1120 gga gat aaa ata ctt gag gtg tct gga gta gat ttg cag aat gcc tca    3525
Gly Asp Lys Ile Leu Glu Val Ser Gly Val Asp Leu Gln Asn Ala Ser
        1125                1130                1135 cac agc gaa gca gtt gag gcc att aag aat gca gga aac cct gtg gtg    3573
His Ser Glu Ala Val Glu Ala Ile Lys Asn Ala Gly Asn Pro Val Val
    1140                1145                1150 ttc att gtt cag agt ttg tca tcc act cca cga gtc att cct aat gta    3621
Phe Ile Val Gln Ser Leu Ser Ser Thr Pro Arg Val Ile Pro Asn Val
1155                1160                1165 cat aac aag gcc aac aaa atc acc agt aac cag aac cag gac acc caa    3669
His Asn Lys Ala Asn Lys Ile Thr Ser Asn Gln Asn Gln Asp Thr Gln
```

```
                    1170                1175                1180                1185
gaa aag aaa gaa aag agg caa gga act gct cca ccg cca atg aaa ctt        3717
Glu Lys Lys Glu Lys Arg Gln Gly Thr Ala Pro Pro Pro Met Lys Leu
                1190                1195                1200 cct cct cct tat aaa gct ctg act gat gac agt gat gaa aat gaa gaa        3765
Pro Pro Pro Tyr Lys Ala Leu Thr Asp Asp Ser Asp Glu Asn Glu Glu
            1205                1210                1215 gaa gat gcc ttt acc gac caa aaa atc aga caa aga tat gca gat ctg        3813
Glu Asp Ala Phe Thr Asp Gln Lys Ile Arg Gln Arg Tyr Ala Asp Leu
        1220                1225                1230 cct gga gaa ctg cac att att gaa ctt gaa aaa gat aag aat gga ctt        3861
Pro Gly Glu Leu His Ile Ile Glu Leu Glu Lys Asp Lys Asn Gly Leu
    1235                1240                1245 gga ctc agc ctt gct ggt aat aaa gac cga tca cgc atg agc ata ttt        3909
Gly Leu Ser Leu Ala Gly Asn Lys Asp Arg Ser Arg Met Ser Ile Phe
1250                1255                1260                1265 gtg gtg gga att aac ccg gaa gga cct gct gcc gca gat gga cga atg        3957
Val Val Gly Ile Asn Pro Glu Gly Pro Ala Ala Ala Asp Gly Arg Met
            1270                1275                1280 cat att gga gat gaa ctc tta gag ata aac aat cag att ctg tat gga        4005
His Ile Gly Asp Glu Leu Leu Glu Ile Asn Asn Gln Ile Leu Tyr Gly
        1285                1290                1295 aga agt cac caa aat gca tct gcc att att aag act gcc cca tca aag        4053
Arg Ser His Gln Asn Ala Ser Ala Ile Ile Lys Thr Ala Pro Ser Lys
    1300                1305                1310 gtc aag ctg gtt ttc atc aga aac gag gat gca gtc aat cag atg gcc        4101
Val Lys Leu Val Phe Ile Arg Asn Glu Asp Ala Val Asn Gln Met Ala
1315                1320                1325 gtt act ccc ttt cca gtg cca tca agt tct cca tct tct att gag gat        4149
Val Thr Pro Phe Pro Val Pro Ser Ser Ser Pro Ser Ser Ile Glu Asp
            1330                1335                1340                1345 cag agc ggc acc gaa cct att agt agt gag gaa gat ggc agc ctc gaa        4197
Gln Ser Gly Thr Glu Pro Ile Ser Ser Glu Glu Asp Gly Ser Leu Glu
        1350                1355                1360 gtt ggt att aaa caa ttg cct gaa agt gaa agc ttc aaa ctg gct gtc        4245
Val Gly Ile Lys Gln Leu Pro Glu Ser Glu Ser Phe Lys Leu Ala Val
    1365                1370                1375 agc cag atg aaa cag caa aaa tat cca aca aaa gtc tcc ttc agt tca        4293
Ser Gln Met Lys Gln Gln Lys Tyr Pro Thr Lys Val Ser Phe Ser Ser
1380                1385                1390 caa gag ata cca tta gca cca gct tca tca tac cat tca aca gat gca        4341
Gln Glu Ile Pro Leu Ala Pro Ala Ser Ser Tyr His Ser Thr Asp Ala
            1395                1400                1405 gac ttc aca ggc tat ggt ggt ttc cag gct cct ctg tca gtg gac ccc        4389
Asp Phe Thr Gly Tyr Gly Gly Phe Gln Ala Pro Leu Ser Val Asp Pro
1410                1415                1420                1425 gca acg tgt ccc att gtc cct gga cag gaa atg att ata gaa ata tcc        4437
Ala Thr Cys Pro Ile Val Pro Gly Gln Glu Met Ile Ile Glu Ile Ser
        1430                1435                1440 aag gga cgt tca ggg ctt ggt ctc agc att gtg gga gga aaa gac aca        4485
Lys Gly Arg Ser Gly Leu Gly Leu Ser Ile Val Gly Gly Lys Asp Thr
    1445                1450                1455 ccc ttg aat gct ata gtt atc cat gaa gtc tat gaa gaa ggg gca gca        4533
Pro Leu Asn Ala Ile Val Ile His Glu Val Tyr Glu Glu Gly Ala Ala
1460                1465                1470 gcc aga gat gga aga ctt tgg gct ggt gac cag ata tta gag gtt aat        4581
Ala Arg Asp Gly Arg Leu Trp Ala Gly Asp Gln Ile Leu Glu Val Asn
    1475                1480                1485 ggg gtt gac ctg agg aac tcc agc cac gaa gaa gcc atc aca gcc ctg        4629
```

```
Gly Val Asp Leu Arg Asn Ser Ser His Glu Glu Ala Ile Thr Ala Leu
1490                1495                1500                1505 agg cag acc ccc cag aag gtg cgg ctg gtg gtg tat aga gat gaa gca         4677
Arg Gln Thr Pro Gln Lys Val Arg Leu Val Val Tyr Arg Asp Glu Ala
            1510                1515                1520 cac tac cgg gat gag gag aac ttg gag att ttc cct gtg gat ctg cag         4725
His Tyr Arg Asp Glu Glu Asn Leu Glu Ile Phe Pro Val Asp Leu Gln
        1525                1530                1535 aag aaa gct ggc cgg ggc ctg ggc ctg agc atc gtt ggg aaa cga aat         4773
Lys Lys Ala Gly Arg Gly Leu Gly Leu Ser Ile Val Gly Lys Arg Asn
    1540                1545                1550 gga agc gga gtg ttt att tct gac atc gtg aaa ggc gga gcc gca gac         4821
Gly Ser Gly Val Phe Ile Ser Asp Ile Val Lys Gly Gly Ala Ala Asp
1555                1560                1565 ctg gat ggg aga ttg att cag gga gat cag atc tta tct gtg aat ggg         4869
Leu Asp Gly Arg Leu Ile Gln Gly Asp Gln Ile Leu Ser Val Asn Gly
1570                1575                1580                1585 gag gac atg aga aat gcc tca cag gag aca gtg gcc acc atc ctc aag         4917
Glu Asp Met Arg Asn Ala Ser Gln Glu Thr Val Ala Thr Ile Leu Lys
        1590                1595                1600 tgt gca cag gga ctt gtg cag cta gag att gga aga ctc cga gct ggt         4965
Cys Ala Gln Gly Leu Val Gln Leu Glu Ile Gly Arg Leu Arg Ala Gly
            1605                1610                1615 tcc tgg acc tcc gca agg acg aca tca cag aac agt cag ggt agt cag         5013
Ser Trp Thr Ser Ala Arg Thr Thr Ser Gln Asn Ser Gln Gly Ser Gln
                1620                1625                1630 cag agt gca cac agc agc tgt cat ccc tcc ttc gct cct gtc atc act         5061
Gln Ser Ala His Ser Ser Cys His Pro Ser Phe Ala Pro Val Ile Thr
            1635                1640                1645 ggc ctg caa aac ctg gtt ggc aca aaa aga gtt tca gat cct tcc cag         5109
Gly Leu Gln Asn Leu Val Gly Thr Lys Arg Val Ser Asp Pro Ser Gln
1650                1655                1660                1665 aaa aat tca ggc aca gat atg gaa cca agg act gtt gag ata aac agg         5157
Lys Asn Ser Gly Thr Asp Met Glu Pro Arg Thr Val Glu Ile Asn Arg
        1670                1675                1680 gag ctc agt gat gcc ctt gga atc agt att gct gga gga aga gga agt         5205
Glu Leu Ser Asp Ala Leu Gly Ile Ser Ile Ala Gly Gly Arg Gly Ser
            1685                1690                1695 ccc tta gga gat atc ccc gta ttt att gcc atg att cag gct agc gga         5253
Pro Leu Gly Asp Ile Pro Val Phe Ile Ala Met Ile Gln Ala Ser Gly
        1700                1705                1710 gtg gcc gca cgg aca cag aag ctt aaa gtt gga gat cgg att gtc agc         5301
Val Ala Ala Arg Thr Gln Lys Leu Lys Val Gly Asp Arg Ile Val Ser
1715                1720                1725 att aac ggg caa cct ttg gat ggg ctg tct cac gcg gat gtg gtt aat         5349
Ile Asn Gly Gln Pro Leu Asp Gly Leu Ser His Ala Asp Val Val Asn
1730                1735                1740                1745 ctg ctg aag aat gcc tac ggg cgc att atc ctg cag gtt gta gca gat         5397
Leu Leu Lys Asn Ala Tyr Gly Arg Ile Ile Leu Gln Val Val Ala Asp
        1750                1755                1760 acc aat ata agc gcc ata gca gct cag ctt gaa aac atg tct aca ggc         5445
Thr Asn Ile Ser Ala Ile Ala Ala Gln Leu Glu Asn Met Ser Thr Gly
            1765                1770                1775 tac cac ctt ggt tcg ccc act gct gaa cac cat cca gaa gac aca gaa         5493
Tyr His Leu Gly Ser Pro Thr Ala Glu His His Pro Glu Asp Thr Glu
        1780                1785                1790 aca cct cca cct aag att att act ttg gag aaa ggc tct gaa ggc ttg         5541
Thr Pro Pro Pro Lys Ile Ile Thr Leu Glu Lys Gly Ser Glu Gly Leu
    1795                1800                1805
```

```
ggg ttt agt att gta ggg ggt tat gga agt ccc cat gga gac ctg cca    5589
Gly Phe Ser Ile Val Gly Gly Tyr Gly Ser Pro His Gly Asp Leu Pro
1810            1815                1820                1825 att tat gtc aag act gta ttt gca aag gga gca gct gca gat gac ggc    5637
Ile Tyr Val Lys Thr Val Phe Ala Lys Gly Ala Ala Ala Asp Asp Gly
        1830                1835                1840 cga tta aaa cga ggg gat cag att tta gct gtt aat ggc gag acc ctg    5685
Arg Leu Lys Arg Gly Asp Gln Ile Leu Ala Val Asn Gly Glu Thr Leu
            1845                1850                1855 gaa ggt gtt act cat gag caa gca gtc gcc att cta aaa cac cag aga    5733
Glu Gly Val Thr His Glu Gln Ala Val Ala Ile Leu Lys His Gln Arg
        1860                1865                1870 ggg act gta acc tta act gtg ctg tcatgagcct cgggcctgat cacaagatag   5787
Gly Thr Val Thr Leu Thr Val Leu
    1875                1880 atgttgttgt ttagaatatc cacaggcaga tgaagttctg agtgggtat              5836

<210> SEQ ID NO 3
<211> LENGTH: 1881
<212> TYPE: PRT
<213> ORGANISM: Homo sapiens

<400> SEQUENCE: 3

Met Pro Glu Asn Pro Ala Thr Asp Lys Leu Gln Val Leu Gln Val Leu
 1               5                  10                  15

Asp Arg Leu Lys Met Lys Leu Gln Glu Lys Gly Asp Thr Ser Gln Asn
                20                  25                  30

Glu Lys Leu Ser Met Phe Tyr Glu Thr Leu Lys Ser Pro Leu Phe Asn
            35                  40                  45

Gln Ile Leu Thr Leu Gln Gln Ser Ile Lys Gln Leu Lys Gly Gln Leu
        50                  55                  60

Asn His Ile Pro Ser Asp Cys Ser Ala Asn Phe Asp Phe Ser Arg Lys
 65                 70                  75                  80

Gly Leu Leu Val Phe Thr Asp Gly Ser Ile Thr Asn Gly Asn Val His
                85                  90                  95

Arg Pro Ser Asn Asn Ser Thr Val Ser Gly Leu Phe Pro Trp Thr Pro
            100                 105                 110

Lys Leu Gly Asn Glu Asp Phe Asn Ser Val Ile Gln Met Ala Gln
        115                 120                 125

Gly Arg Gln Ile Glu Tyr Ile Asp Ile Glu Arg Pro Ser Thr Gly Gly
    130                 135                 140

Leu Gly Phe Ser Val Val Ala Leu Arg Ser Gln Asn Leu Gly Lys Val
145                 150                 155                 160

Asp Ile Phe Val Lys Asp Val Gln Pro Gly Ser Val Ala Asp Arg Asp
                165                 170                 175

Gln Arg Leu Lys Glu Asn Asp Gln Ile Leu Ala Ile Asn His Thr Pro
            180                 185                 190

Leu Asp Gln Asn Ile Ser His Gln Gln Ala Ile Ala Leu Leu Gln Gln
        195                 200                 205

Thr Thr Gly Ser Leu Arg Leu Ile Val Ala Arg Glu Pro Val His Thr
    210                 215                 220

Lys Ser Ser Thr Ser Ser Ser Leu Asn Asp Thr Thr Leu Pro Glu Thr
225                 230                 235                 240

Val Cys Trp Gly His Val Glu Glu Val Glu Leu Ile Asn Asp Gly Ser
                245                 250                 255

Gly Leu Gly Phe Gly Ile Val Gly Gly Lys Thr Ser Gly Val Val Val
```

```
                260                 265                 270
Arg Thr Ile Val Pro Gly Gly Leu Ala Asp Arg Asp Gly Arg Leu Gln
                    275                 280                 285

Thr Gly Asp His Ile Leu Lys Ile Gly Gly Thr Asn Val Gln Gly Met
        290                 295                 300

Thr Ser Glu Gln Val Ala Gln Val Leu Arg Asn Cys Gly Asn Ser Val
305                 310                 315                 320

Arg Met Leu Val Ala Arg Asp Pro Ala Gly Asp Ile Ser Val Thr Pro
                325                 330                 335

Pro Ala Pro Ala Ala Leu Pro Val Ala Leu Pro Thr Val Ala Ser Lys
                340                 345                 350

Gly Pro Gly Ser Asp Ser Ser Leu Phe Glu Thr Tyr Asn Val Glu Leu
                355                 360                 365

Val Arg Lys Asp Gly Gln Ser Leu Gly Ile Arg Ile Val Gly Tyr Val
        370                 375                 380

Gly Thr Ser His Thr Gly Glu Ala Ser Gly Ile Tyr Val Lys Ser Val
385                 390                 395                 400

Ile Pro Gly Ser Ala Ala Tyr His Asn Gly His Ile Gln Val Asn Asp
                    405                 410                 415

Lys Ile Val Ala Val Asp Gly Val Asn Ile Gln Gly Phe Ala Asn His
                420                 425                 430

Asp Val Val Glu Val Leu Arg Asn Ala Gly Gln Val Val His Leu Thr
                435                 440                 445

Leu Val Arg Arg Lys Thr Ser Ser Thr Ser Pro Leu Glu Pro Pro
        450                 455                 460

Ser Asp Arg Gly Thr Val Val Glu Pro Leu Lys Pro Ala Leu Phe
465                 470                 475                 480

Leu Thr Gly Ala Val Glu Thr Glu Thr Asn Val Asp Gly Glu Asp Glu
                    485                 490                 495

Glu Ile Lys Glu Arg Ile Asp Thr Leu Lys Asn Asp Asn Ile Gln Ala
                500                 505                 510

Leu Glu Lys Leu Glu Lys Val Pro Asp Ser Pro Glu Asn Glu Leu Lys
        515                 520                 525

Ser Arg Trp Glu Asn Leu Leu Gly Pro Asp Tyr Glu Val Met Val Ala
530                 535                 540

Thr Leu Asp Thr Gln Ile Ala Asp Asp Ala Glu Leu Gln Lys Tyr Ser
545                 550                 555                 560

Lys Leu Leu Pro Ile His Thr Leu Arg Leu Gly Val Glu Val Asp Ser
                    565                 570                 575

Phe Asp Gly His His Tyr Ile Ser Ser Ile Val Ser Gly Gly Pro Val
                580                 585                 590

Asp Thr Leu Gly Leu Leu Gln Pro Glu Asp Glu Leu Leu Glu Val Asn
        595                 600                 605

Gly Met Gln Leu Tyr Gly Lys Ser Arg Arg Glu Ala Val Ser Phe Leu
        610                 615                 620

Lys Glu Val Pro Pro Phe Thr Leu Val Cys Cys Arg Arg Leu Phe
625                 630                 635                 640

Asp Asp Glu Ala Ser Val Asp Glu Pro Arg Arg Thr Glu Thr Ser Leu
                645                 650                 655

Pro Glu Thr Glu Val Asp His Asn Met Asp Val Asn Thr Glu Glu Asp
                660                 665                 670

Asp Asp Gly Glu Leu Ala Leu Trp Ser Pro Glu Val Lys Ile Val Glu
        675                 680                 685
```

```
Leu Val Lys Asp Cys Lys Gly Leu Gly Phe Ser Ile Leu Asp Tyr Gln
    690                 695                 700

Asp Pro Leu Asp Pro Thr Arg Ser Val Ile Val Ile Arg Ser Leu Val
705                 710                 715                 720

Ala Asp Gly Val Ala Glu Arg Ser Gly Gly Leu Leu Pro Gly Asp Arg
                725                 730                 735

Leu Val Ser Val Asn Glu Tyr Cys Leu Asp Asn Thr Ser Leu Ala Glu
                740                 745                 750

Ala Val Glu Ile Leu Lys Ala Val Pro Pro Gly Leu Val His Leu Gly
            755                 760                 765

Ile Cys Lys Pro Leu Val Glu Asp Asn Glu Glu Ser Cys Tyr Ile
770                 775                 780

Leu His Ser Ser Ser Asn Glu Asp Lys Thr Glu Phe Ser Gly Thr Ile
785                 790                 795                 800

His Asp Ile Asn Ser Ser Leu Ile Leu Glu Ala Pro Lys Gly Phe Arg
                805                 810                 815

Asp Glu Pro Tyr Phe Lys Glu Glu Leu Val Asp Glu Pro Phe Leu Asp
                820                 825                 830

Leu Gly Lys Ser Phe His Ser Gln Gln Lys Glu Ile Glu Gln Ser Lys
                835                 840                 845

Glu Ala Trp Glu Met His Glu Phe Leu Thr Pro Arg Leu Gln Glu Met
850                 855                 860

Asp Glu Glu Arg Glu Met Leu Val Asp Glu Glu Tyr Glu Leu Tyr Gln
865                 870                 875                 880

Asp Pro Ser Pro Ser Met Glu Leu Tyr Pro Leu Ser His Ile Gln Glu
                885                 890                 895

Ala Thr Pro Val Pro Ser Val Asn Glu Leu His Phe Gly Thr Gln Trp
                900                 905                 910

Leu His Asp Asn Glu Pro Ser Glu Ser Gln Glu Ala Arg Thr Gly Arg
                915                 920                 925

Thr Val Tyr Ser Gln Glu Ala Gln Pro Tyr Gly Tyr Cys Pro Glu Asn
    930                 935                 940

Val Met Lys Glu Asn Phe Val Met Glu Ser Leu Pro Ser Val Pro Ser
945                 950                 955                 960

Thr Glu Gly Asn Ser Gln Gln Gly Arg Phe Asp Asp Leu Glu Asn Leu
                965                 970                 975

Asn Ser Leu Ala Lys Thr Ser Asp Leu Gly Met Ile Pro Asn Asp
                980                 985                 990

Val Gln Gly Pro Ser Leu Leu Ile Asp Leu Pro Val Val Ala Gln Arg
            995                 1000                1005

Arg Glu Gln Glu Asp Leu Pro Leu Tyr Gln His Gln Ala Thr Arg Val
    1010                1015                1020

Ile Ser Lys Ala Ser Ala Tyr Thr Gly Met Leu Ser Ser Arg Tyr Ala
025                 1030                1035                1040

Thr Asp Thr Cys Glu Leu Pro Arg Glu Glu Gly Glu Gly Glu Glu
                1045                1050                1055

Thr Pro Asn Phe Ser His Trp Gly Pro Pro Arg Ile Val Glu Ile Phe
                1060                1065                1070

Arg Glu Pro Asn Val Ser Leu Gly Ile Ser Ile Val Gly Gly Gln Thr
            1075                1080                1085

Val Ile Lys Arg Leu Lys Asn Gly Glu Glu Leu Lys Gly Ile Phe Ile
            1090                1095                1100
```

-continued

```
Lys Gln Val Leu Glu Asp Ser Pro Ala Gly Lys Thr Asn Ala Leu Lys
105             1110             1115             1120

Thr Gly Asp Lys Ile Leu Glu Val Ser Gly Val Asp Leu Gln Asn Ala
            1125             1130             1135

Ser His Ser Glu Ala Val Glu Ala Ile Lys Asn Ala Gly Asn Pro Val
            1140             1145             1150

Val Phe Ile Val Gln Ser Leu Ser Ser Thr Pro Arg Val Ile Pro Asn
            1155             1160             1165

Val His Asn Lys Ala Asn Lys Ile Thr Ser Asn Gln Asn Gln Asp Thr
    1170             1175             1180

Gln Glu Lys Lys Glu Lys Arg Gln Gly Thr Ala Pro Pro Met Lys
185             1190             1195             1200

Leu Pro Pro Pro Tyr Lys Ala Leu Thr Asp Asp Ser Asp Glu Asn Glu
            1205             1210             1215

Glu Glu Asp Ala Phe Thr Asp Gln Lys Ile Arg Gln Arg Tyr Ala Asp
            1220             1225             1230

Leu Pro Gly Glu Leu His Ile Ile Glu Leu Glu Lys Asp Lys Asn Gly
            1235             1240             1245

Leu Gly Leu Ser Leu Ala Gly Asn Lys Asp Arg Ser Arg Met Ser Ile
            1250             1255             1260

Phe Val Val Gly Ile Asn Pro Glu Gly Pro Ala Ala Ala Asp Gly Arg
265             1270             1275             1280

Met His Ile Gly Asp Glu Leu Leu Glu Ile Asn Asn Gln Ile Leu Tyr
            1285             1290             1295

Gly Arg Ser His Gln Asn Ala Ser Ala Ile Ile Lys Thr Ala Pro Ser
            1300             1305             1310

Lys Val Lys Leu Val Phe Ile Arg Asn Glu Asp Ala Val Asn Gln Met
            1315             1320             1325

Ala Val Thr Pro Phe Pro Val Pro Ser Ser Pro Ser Ser Ile Glu
            1330             1335             1340

Asp Gln Ser Gly Thr Glu Pro Ile Ser Ser Glu Glu Asp Gly Ser Leu
345             1350             1355             1360

Glu Val Gly Ile Lys Gln Leu Pro Glu Ser Glu Ser Phe Lys Leu Ala
            1365             1370             1375

Val Ser Gln Met Lys Gln Gln Lys Tyr Pro Thr Lys Val Ser Phe Ser
            1380             1385             1390

Ser Gln Glu Ile Pro Leu Ala Pro Ala Ser Ser Tyr His Ser Thr Asp
            1395             1400             1405

Ala Asp Phe Thr Gly Tyr Gly Gly Phe Gln Ala Pro Leu Ser Val Asp
            1410             1415             1420

Pro Ala Thr Cys Pro Ile Val Pro Gly Gln Glu Met Ile Ile Glu Ile
425             1430             1435             1440

Ser Lys Gly Arg Ser Gly Leu Gly Leu Ser Ile Val Gly Gly Lys Asp
            1445             1450             1455

Thr Pro Leu Asn Ala Ile Val Ile His Glu Val Tyr Glu Glu Gly Ala
            1460             1465             1470

Ala Ala Arg Asp Gly Arg Leu Trp Ala Gly Asp Gln Ile Leu Glu Val
            1475             1480             1485

Asn Gly Val Asp Leu Arg Asn Ser Ser His Glu Glu Ala Ile Thr Ala
            1490             1495             1500

Leu Arg Gln Thr Pro Gln Lys Val Arg Leu Val Val Tyr Arg Asp Glu
505             1510             1515             1520

Ala His Tyr Arg Asp Glu Glu Asn Leu Glu Ile Phe Pro Val Asp Leu
```

```
                        1525                1530                1535

Gln Lys Lys Ala Gly Arg Gly Leu Gly Leu Ser Ile Val Gly Lys Arg
            1540                1545                1550

Asn Gly Ser Gly Val Phe Ile Ser Asp Ile Val Lys Gly Gly Ala Ala
        1555                1560                1565

Asp Leu Asp Gly Arg Leu Ile Gln Gly Asp Gln Ile Leu Ser Val Asn
    1570                1575                1580

Gly Glu Asp Met Arg Asn Ala Ser Gln Glu Thr Val Ala Thr Ile Leu
585                 1590                1595                1600

Lys Cys Ala Gln Gly Leu Val Gln Leu Glu Ile Gly Arg Leu Arg Ala
            1605                1610                1615

Gly Ser Trp Thr Ser Ala Arg Thr Thr Ser Gln Asn Ser Gln Gly Ser
        1620                1625                1630

Gln Gln Ser Ala His Ser Ser Cys His Pro Ser Phe Ala Pro Val Ile
    1635                1640                1645

Thr Gly Leu Gln Asn Leu Val Gly Thr Lys Arg Val Ser Asp Pro Ser
    1650                1655                1660

Gln Lys Asn Ser Gly Thr Asp Met Glu Pro Arg Thr Val Glu Ile Asn
665                 1670                1675                1680

Arg Glu Leu Ser Asp Ala Leu Gly Ile Ser Ile Ala Gly Gly Arg Gly
            1685                1690                1695

Ser Pro Leu Gly Asp Ile Pro Val Phe Ile Ala Met Ile Gln Ala Ser
        1700                1705                1710

Gly Val Ala Ala Arg Thr Gln Lys Leu Lys Val Gly Asp Arg Ile Val
    1715                1720                1725

Ser Ile Asn Gly Gln Pro Leu Asp Gly Leu Ser His Ala Asp Val Val
    1730                1735                1740

Asn Leu Leu Lys Asn Ala Tyr Gly Arg Ile Ile Leu Gln Val Val Ala
745                 1750                1755                1760

Asp Thr Asn Ile Ser Ala Ile Ala Ala Gln Leu Glu Asn Met Ser Thr
            1765                1770                1775

Gly Tyr His Leu Gly Ser Pro Thr Ala Glu His His Pro Glu Asp Thr
        1780                1785                1790

Glu Thr Pro Pro Lys Ile Ile Thr Leu Glu Lys Gly Ser Glu Gly
    1795                1800                1805

Leu Gly Phe Ser Ile Val Gly Gly Tyr Gly Ser Pro His Gly Asp Leu
    1810                1815                1820

Pro Ile Tyr Val Lys Thr Val Phe Ala Lys Gly Ala Ala Ala Asp Asp
825                 1830                1835                1840

Gly Arg Leu Lys Arg Gly Asp Gln Ile Leu Ala Val Asn Gly Glu Thr
            1845                1850                1855

Leu Glu Gly Val Thr His Glu Gln Ala Val Ala Ile Leu Lys His Gln
        1860                1865                1870

Arg Gly Thr Val Thr Leu Thr Val Leu
    1875                1880

<210> SEQ ID NO 4
<211> LENGTH: 290
<212> TYPE: DNA
<213> ORGANISM: Mus musculus
<220> FEATURE:
<221> NAME/KEY: CDS
<222> LOCATION: (105)..(290)

<400> SEQUENCE: 4
```

```
acttccgcca ggtgaggagg ccgtccgtgc ccgcagcccc ggggctccca ccccgccgtc         60
gcccgatcag acttttgga agtgattgaa agaatatcc caaa atg cct gaa aac          116
                                             Met Pro Glu Asn
                                              1 cct gct gca gag aag atg cag gtc ctg cag gtc ctg gat cgc ctt cga         164
Pro Ala Ala Glu Lys Met Gln Val Leu Gln Val Leu Asp Arg Leu Arg
 5           10                  15                      20 gga aag ctg cag gag aag gga gac acg acg cag aac gag aag ctg tct         212
Gly Lys Leu Gln Glu Lys Gly Asp Thr Thr Gln Asn Glu Lys Leu Ser
             25                  30                  35 gcg ttc tac gag acg ctg aag agc cct ctc ttc aac cag atc ctt aca         260
Ala Phe Tyr Glu Thr Leu Lys Ser Pro Leu Phe Asn Gln Ile Leu Thr
         40                  45                  50 ctg cag cag tcc atc aag cag ctg aag gga                                 290
Leu Gln Gln Ser Ile Lys Gln Leu Lys Gly
         55                  60
```

<210> SEQ ID NO 5
<211> LENGTH: 62
<212> TYPE: PRT
<213> ORGANISM: Mus musculus

<400> SEQUENCE: 5

Met Pro Glu Asn Pro Ala Ala Glu Lys Met Gln Val Leu Gln Val Leu
 1               5                  10                  15

Asp Arg Leu Arg Gly Lys Leu Gln Glu Lys Gly Asp Thr Thr Gln Asn
             20                  25                  30

Glu Lys Leu Ser Ala Phe Tyr Glu Thr Leu Lys Ser Pro Leu Phe Asn
         35                  40                  45

Gln Ile Leu Thr Leu Gln Gln Ser Ile Lys Gln Leu Lys Gly
     50                  55                  60

<210> SEQ ID NO 6
<211> LENGTH: 15
<212> TYPE: PRT
<213> ORGANISM: Homo sapiens

<400> SEQUENCE: 6

Asn Glu Pro Phe Asp Glu Asp Gln His Thr Gln Ile Thr Lys Val
 1               5                  10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence:SH3 Binding
      Protein PDZ Domain

<400> SEQUENCE: 7

Ser Gly Ser Gly Ile Leu Ala Pro Pro Val Pro Pro Arg Asn Thr Arg
 1               5                  10                  15

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence:AF6 PDZ
      Binding Protein

<400> SEQUENCE: 8

Ser Gly Asp Asp Gly Asp Asp Pro Phe Leu Gln Tyr Glu Phe Tyr Val

<210> SEQ ID NO 9
<211> LENGTH: 16
<212> TYPE: PRT
<213> ORGANISM: Homo sapiens

<400> SEQUENCE: 9

Glu Asn Glu Pro Phe Asp Glu Asp Gln His Thr Gln Ile Thr Lys Val
 1               5                  10                  15

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 10
caggtgaggc agggccgaca                                              20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 11
ctacagtagg cagggcaaca gg                                           22

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 12
gttttcccag tcacgacgcg ggctcccacc tgctcctc                          38

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 13
aggaaacagc tatgaccatg tgaacactaa caaacctttc c                      41

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 14
gttttcccag tcacgacgtc aactcaacca tataccctca                        40

```
<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 15
aggaaacagc tatgaccatg gctggacatc cttcacgaag                          40

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 16
gttttcccag tcacgacggc cttggattca gtgtggtg                            38

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 17
aggaaacagc tatgaccatc cccaacaaac tgtttcaggc                          40

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 18
gttttcccag tcacgacgcc agggaaccag tccacaca                            38

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 19
aggaaacagc tatgaccatc ctgactgaat tcccacag                            38

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 20
tcctggagga ttagcagatc gag                                            23

<210> SEQ ID NO 21
```

<211> LENGTH: 24
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 21
ggtaatccaa aatgctgaat ccca                                          24

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 22
gttttcccag tcacgacgaa gattggtggc acaaacgtg                          39

<210> SEQ ID NO 23
<211> LENGTH: 41
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 23
aggaaacagc tatgaccata gcactgccag gtattatact t                       41

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 24
gttttcccag tcacgacgag aattgttggc tatgttggaa c                       41

<210> SEQ ID NO 25
<211> LENGTH: 41
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 25
aggaaacagc tatgaccatg ctccagttag aaagagagct g                       41

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 26
gttttcccag tcacgacgac atcctcatct acttctcca                          39

<210> SEQ ID NO 27
<211> LENGTH: 40

```
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 27
aggaaacagc tatgaccata actcagcatc atctgcaatc                              40

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 28
gttttcccag tcacgacggg aaaacctgtt gggtcctg                                38

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 29
aggaaacagc tatgaccatc gacagcaaac caaagtaaaa gg                           42

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 30
gtggattcct ttgatgggca cc                                                 22

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 31
ctttgagcca caacaggaag gtc                                                23

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 32
gttttcccag tcacgacgtg agctgcttga ggtcaatgg                               39

<210> SEQ ID NO 33
<211> LENGTH: 39
<212> TYPE: DNA
```

```
<213> ORGANISM: Artificial Sequence
<220> FEATURE:
<223> OTHER INFORMATION: Description of Artificial Sequence:MMSC1
      Primers

<400> SEQUENCE: 33
aggaaacagc tatgaccatc taaagggtcc tggtaatcc                              39

<210> SEQ ID NO 34
<211> LENGTH: 39
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 34
gttttcccag tcacgacgcc cctgaagtca agattgttg                              39

<210> SEQ ID NO 35
<211> LENGTH: 44
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 35
aggaaacagc tatgaccata caactttctt cttcattatc ttcc                        44

<210> SEQ ID NO 36
<211> LENGTH: 38
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 36
gttttcccag tcacgacgga aatattgaaa gctgtgcc                               38

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 37
aggaaacagc tatgaccatg tcagaaattc atgcatctcc                             40

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 38
gttttcccag tcacgacgaa agtctttcca ttcccaacaa                             40

<210> SEQ ID NO 39
<211> LENGTH: 39
<212> TYPE: DNA
<213> ORGANISM: Artificial Sequence
```

```
<220> FEATURE:
<223> OTHER INFORMATION: Description of Artificial Sequence:MMSC1
      Primers

<400> SEQUENCE: 39
aggaaacagc tatgaccatc catacggctg tgcctcctg                              39

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 40
gagttatatc aagatccctc accat                                             25

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 41
caaatatgct catgcgtgat cgg                                               23

<210> SEQ ID NO 42
<211> LENGTH: 41
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 42
gttttcccag tcacgacgtt cactttggta cacagtggtt g                           41

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 43
aggaaacagc tatgaccata aatcttcttg ctccctcctt                             40

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 44
gttttcccag tcacgacgcc cgaatgatgt ccaaggtcc                              39

<210> SEQ ID NO 45
<211> LENGTH: 40
<212> TYPE: DNA
<213> ORGANISM: Artificial Sequence
<220> FEATURE:
```

<223> OTHER INFORMATION: Description of Artificial Sequence:MMSC1
      Primers

<400> SEQUENCE: 45
aggaaacagc tatgaccatg tccaccaaca atactgatcc                              40

<210> SEQ ID NO 46
<211> LENGTH: 38
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 46
gttttcccag tcacgacgag ccactggggt ccaccgag                                38

<210> SEQ ID NO 47
<211> LENGTH: 41
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 47
aggaaacagc tatgaccata ctcgtggagt ggatgacaaa c                            41

<210> SEQ ID NO 48
<211> LENGTH: 38
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 48
gttttcccag tcacgacgca gttgaggcca ttaagaat                                38

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 49
aggaaacagc tatgaccatc aagttcaata atgtgcagtt ct                           42

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 50
cgccaatgaa acttcctcct cct                                                23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence:MMSC1

Primers

<400> SEQUENCE: 51
tctcctgtga ggcatttctc atg                                              23

<210> SEQ ID NO 52
<211> LENGTH: 41
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 52
gttttcccag tcacgacgcc tttaccgacc aaaaaatcag a                          41

<210> SEQ ID NO 53
<211> LENGTH: 38
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 53
aggaaacagc tatgaccatc tgattgactg catcctcg                              38

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 54
gttttcccag tcacgacgca tctgccatta ttaagactgc                            40

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 55
aggaaacagc tatgaccatg tgaagtctgc atctgttgaa t                          41

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 56
gttttcccag tcacgacgtc caacaaaagt ctccttcagt                            40

<210> SEQ ID NO 57
<211> LENGTH: 40
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 57
aggaaacagc tatgaccata acctctaata tctggtcacc                                40

<210> SEQ ID NO 58
<211> LENGTH: 39
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 58
gttttcccag tcacgacgct atagttatcc atgaagtct                                 39

<210> SEQ ID NO 59
<211> LENGTH: 38
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 59
aggaaacagc tatgaccatc cgcctttcac gatgtcag                                  38

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 60
gaaggtgcgg ctggtggtgt at                                                   22

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 61
cttgctctgt cacccaggct g                                                    21

<210> SEQ ID NO 62
<211> LENGTH: 38
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 62
gttttcccag tcacgacggg cctgagcatc gttgggaa                                  38

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence:MMSC1
      Primers

```
-continued

<400> SEQUENCE: 63
aggaaacagc tatgaccata accaggtttt gcaggccagt                40

<210> SEQ ID NO 64
<211> LENGTH: 39
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 64
gttttcccag tcacgacgtc agggtagtca gcagagtgc                 39

<210> SEQ ID NO 65
<211> LENGTH: 39
<212> TYPE: DNA
<213> ORGANISM: Artificial Sequence
<220> FEATURE:
<223> OTHER INFORMATION: Description of Artificial Sequence:MMSC1
      Primers

<400> SEQUENCE: 65
aggaaacagc tatgaccatt acccacatcc gcgtgagac                 39
```

MMSC1-AN MMAC1 INTERACTING PROTEIN

CROSS REFERENCE TO RELATED APPLICATION

The present application is related to U.S. provisional patent application Ser. No. 60/071,861, filed Jan. 20, 1998, incorporated herein by reference.

BACKGROUND OF THE INVENTION

The present invention is directed to the MMSC1 gene, its protein product and the use of the protein to (i) detect mutant MMAC1 proteins, (ii) screen for drugs which can be used for suppressing tumor growth and (iii) identify proteins which interact with the MMAC1 gene or are involved in the tumor suppression pathway of the MMAC1 gene.

The publications and other materials used herein to illuminate the background of the invention or provide additional details respecting the practice, are incorporated by reference, and for convenience are respectively grouped in the appended List of References.

A number of genetic alterations are involved in the oncogenesis of glioblastoma multiforme, including inactivation of p53, p16, RB, amplification of the gene encoding epidermal growth factor receptor and several other molecular alterations (Louis & Gusella, 1995). However the most common genetic alteration is the deletion of large regions or an entire copy of chromosome 10 (Fults et al., 1990; Rahseed et al., 1992). Recently, the tumor suppressor gene MMAC1 (Steck et al., 1997), also known as PTEN (Li et al., 1997) or TEP1 (Li & Sun, 1997) was mapped to 10q23 and shown to be mutated in 17–24% of xenografted and primary glioblastomas, 14% of breast cancer samples and 25% of kidney carcinomas (Steck et al., 1997). The mutation frequency in established cell lines of these tumor types is somewhat higher. In addition to this predicted involvement in sporadic cancer, germ-line MMAC1 mutations have been detected in two autosomal dominant disorders, Cowden disease (Nelen et al., 1997; Liaw et al., 1997), a syndrome that confers an elevated risk for tumors of breast, thyroid and skin, and Bannayan-Zonana syndrome (Marsh et al., 1997), a condition characterized by macrocephaly, lipomas, intestinal hamartomatous polyps, vascular malformations and some skin disorders. Mutations of MMAC1 in primary endometrial carcinomas (Kong et al., 1997) and in juvenile polyposis *coli* (Olschwang et al., 1998) have also been seen.

The predicted protein product of the MMAC1 gene has several regions of homology with other proteins. The MMAC1 protein has an animo terminal domain with extensive homology to tensin, a protein that interacts with actin filaments at focal adhesions, and with auxilin, a protein involved in synaptic vesicle transport. The MMAC1 protein also has a region with extensive homology to protein tyrosine phosphatases (Steck et al., 1997; Li et al., 1997). Mutations of MMAC1 in tumors, its cytoplasmic localization (Li & Sun, 1997) and its intrinsic phosphatase activity (Li & Sun, 1997; Myers et al., 1997) suggested that its activity could be important in some aspect of tumor progression, possibly to counteract the oncogenic effect of a specific protein tyrosine kinase. In addition, MMAC1 is rapidly down-regulated by $TGF_\beta$ in cells sensitive to its cell growth and cell adhesion regulatory properties (Li & Sun, 1997).

Experiments on glioma cell growth have shown that MMAC1 is a protein phosphatase that exhibits functional and specific growth-suppressing activity. In such experiments, the introduction of HA-tagged MMAC1 into glioma cells containing endogenous mutant alleles caused growth suppression, but was without effect in cells containing HA-tagged MMAC1 (Furnari et al., 1997). The ectopic expression of MMAC1 alleles, which carried mutations found in primary tumors and have been shown or are expected to inactivate its phosphatase activity, caused little growth suppression (Furnari et al., 1997). Although these activities of MMAC1 are known, the mechanisms of tumor suppression by MMAC1 and the interaction of the MMAC1 protein with other proteins are not well understood.

Many cytosolic signaling proteins and cytoskeletal proteins are composed of modular units of small protein-protein interactive domains that allow reversible and regulated assembly into larger protein complexes. These domains include the Src-homology SH2 and SH3 domains (Schlessinger, 1994; Pawson, 1994), pleckstrin-homology (PH) domains (Lemmon et al., 1996; Shaw, 1996), phosphotyrosine-binding (PTB) domains (Harrison, 1996; van der Greer & Pawson, 1995; Kavanaugh et al., 1995) and postsynaptic density protein, disc-large, zo-1 (PDZ) domain (Woods & Bryant, 1991; Dho et al., 1992; Woods & Bryant, 1993; Kennedy, 1995; Kornau et al., 1995). So far, PDZ domains have been found in more than 50 proteins (Tsunoda et al., 1997), and many proteins have multiple PDZ domains (Pawson & Scott, 1997). For a review of PDZ domains, as well as the other protein-protein interactive domains, see Pawson & Scott (1997).

A distinguishing feature of PDZ domains is their recognition of short peptides at the carboxyl terminal end of proteins. For example, one family of PDZ domains selected peptides with the consensus motif Glu-(Ser/Thr)-Xaa-(Val/Ile) (SEQ ID NO:1) at the carboxy terminus, whereas a second family of PDZ domains selected peptides with hydrophobic or aromatic side chains at the carboxy terminal three residues (Songyang et al., 1997). The presence of multiple PDZ domains in proteins may have at least two important consequences. An individual PDZ-containinig protein could bind several subunits of a particular channel thereby inducing channel aggregations. Furthermore, the individual domains of a protein can have distinct binding specificities thereby inducing the formation of clusters that contain heterogeneous groups of proteins.

One example of this latter consequence of multiple PDZ domains is the InaD protein which contains five PDZ domains and acts as a scaffolding protein to organize the light-activated signaling events in Drosophila (Shieh & Zhui, 1996; Tsunoda et al., 1997). InaD associates through distinct PDZ domains with a calcium channel(TRP), phospholipase C-β (the target of rhodopsin-activated heterotrimeric guanine nucleotide-binding protein (Gqα)) and protein kinase C.

Two further properties of PDZ domains or proteins which contain them may expand their potential activities. First, some PDZ domains may bind internal peptide sequences and, indeed, have a propensity to undergo homotypic or heterotypic interactions with other PDZ domains (Brenman et al., 1996). Second, proteins with PDZ domains frequently contain other interaction modules, including SH3 and LIM domains, and catalytic elements such a tyrosine phosphatase or nitric oxide synthase domains. PDZ domains may therefore both coordinate the localization and clustering of receptors and channels, and provide a bridge to the cytoskeleton or intracellular signaling pathways.

It is desired to determine the mechanisms of tumor suppression for MMAC1 and to identify proteins which interact with the MMAC1 protein. Such proteins can be used to assay for mutated MMAC1 proteins and/or screen potential drugs for suppressing tumor growth and/or identify additional proteins which interact with MMAC1.

SUMMARY OF THE INVENTION

The present invention is directed to the MMSC1 gene, its protein product and the use of the protein to (i) detect mutant MMAC1 proteins, (ii) screen for drugs which can be used for suppressing tumor growth and (iii) identify proteins which interact with the MMAC1 gene or are involved in the tumor suppression pathway of the MMAC1 gene.

Using yeast two-hybrid screening, it has been found MMAC1 binds to a protein herein named MMSC1. The nucleotide sequence is set forth as SEQ ID NO:2, and the amino acid sequence is set forth as SEQ ID NO:3. It has been found MMSC1 has 11 PDZ domains and that one or more of these domains interacts specifically with the three carboxyl terminal amino acids of MMAC1. Specifically, it has been found that PDZ domain number 7 interacts with MMAC1. Since MMSC1 contains 11 PDZ domains and interacts with MMAC1, known tumor suppressor having a region of homology with protein tyrosine phosphatases, MMSC1 acts as a scaffolding protein in a common biochemical pathway with MMAC1. These characteristics indicate that the interaction between MMAC1 and MMSC1 is required for the tumor suppressor activity of MMAC1.

BRIEF DESCRIPTION OF THE FIGURES

FIG. 2 shows an alignment of the first 300 nucleotides of human MMSC1 (H.s._MMSC1) with its translation product (H.s._MMSC1.pep) and the corresponding sequence from the mouse ortholog (M.m._MMSC1; SEQ ID NO:4), as determined from an analysis of the sequence from the above noted clones, with its translation product (M.m._MMSC1.pep; SEQ ID NO:5).

SUMMARY OF SEQUENCE LISTING

Figure 1:
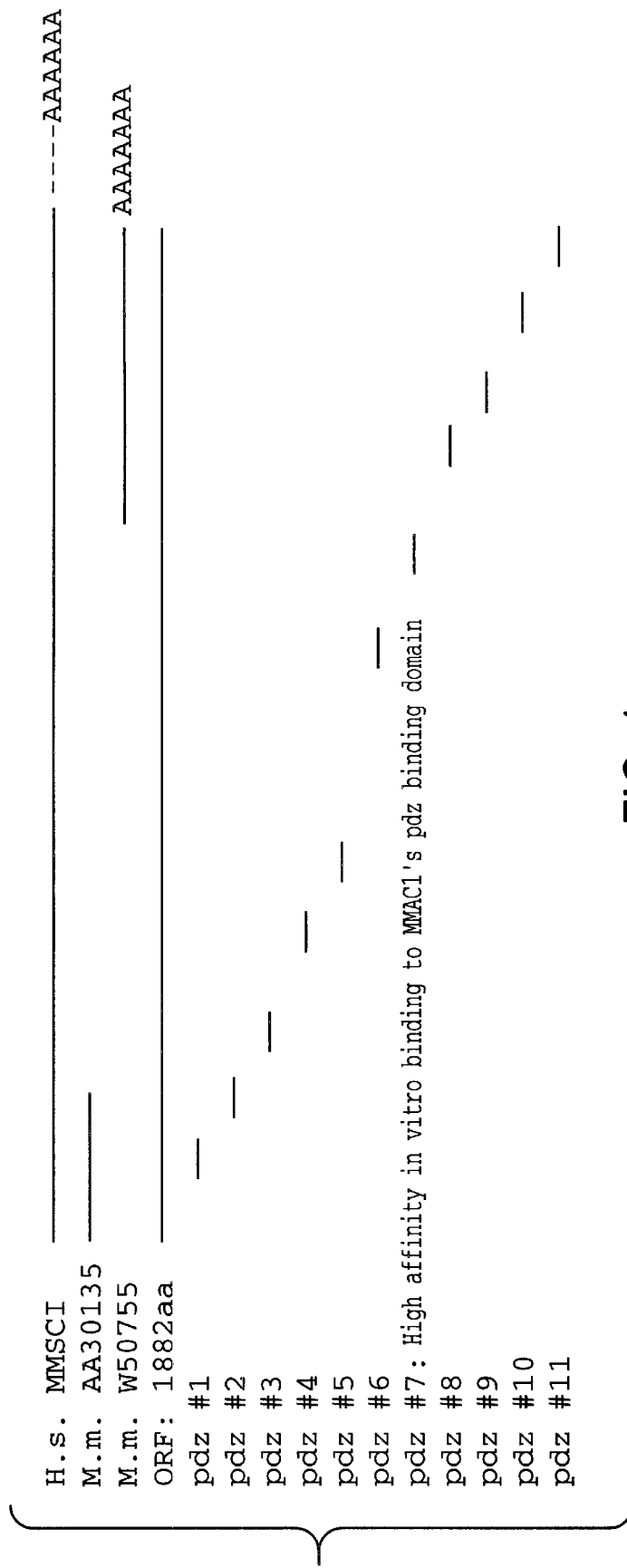
FIG. 1 shows a diagram of MMSC1 indicating the position of the 11 PDZ domains and the overlap of the two mouse cDNA clones.

SEQ ID NO:1 is a consensus motif to which one family of PDZ domains interacts. SEQ ID NO:2 is the nucleotide sequence for the MMSC1 gene. SEQ ID NO:3 is the amino acid sequence for the MMSC1 protein. SEQ ID NO:4 is the nucleotide sequence for the 5' end of a fragment of the mouse homolog. SEQ ID NO:5 is the amino acid sequence for the N-terminus fragment of a mouse homolog. SEQ ID NO:6 is the 15 C-teiminal amino acids of MMAC1. SEQ ID NO:7 is the SH3 binding peptide. SEQ ID NO:8 is the AF6 binding peptide. SEQ ID NO:9 is the MMAC1 binding peptide. SEQ ID NOs:10–65 are primers for PCR amplification of the MMSC1 gene.

DETAILED DESCRIPTION OF THE INVENTION

The present invention is directed to the MMSC1 gene, its protein product and the use of the protein to (i) detect mutant MMAC1 proteins, (ii) screen for drugs which can be used for suppressing tumor growth and (iii) identify proteins which interact with the MMAC1 gene or are involved in the tumor suppression pathway of the MMAC1 gene.

Using yeast two-hybrid screening, it has been found MMAC1 binds to a protein herein named MMSC1. The nucleotide sequence is set forth as SEQ ID NO:2, and the amino acid sequence is set forth as SEQ ID NO:3. It has been found MMSC1 has 11 PDZ domains and that one or more of these domains interacts specifically with the three carboxyl terminal amino acids of MMAC1. Specifically, it has been found that PDZ domain number 7 interacts with MMAC1. Since MMSC1 contains 11 PDZ domains and interacts with MMAC1, a known tumor suppressor having a region of homology with protein tyrosine phosphatases, MMSC1 acts as a scaffolding protein in a common biochemical pathway with MMAC 1. These characteristics indicate that the interaction between MMAC1 and MMSC1 is required for the tumor suppressor activity of MMAC1.

The evidence presented herein shows that the function of MMSC1 is to make a scaffold that binds to MMAC1, the phosphatase substrate(s), and the (probably oncogene) tyrosine kinase(s). Thus, a valuable drug will be one that can prevent binding of either the substrate(s) or the tyrosine kinases(s) to MMSC1.

The yeast two-hybrid screening assay described herein identified two clones encoding bona fide MMAC1 interacting proteins. The clones were identified pzdk5 and pdzk21. A search of GenBank with the sequences of pzdk5 and pdzk21 revealed that they could be assembled with a partial cDNA sequence AJ001306, to generate the complete coding sequence of a gene named MMSC1 set forth in SEQ ID NO:2. dBEST sequences from two mouse cDNA clones (GenBank accession numbers AA030135 and W50755; IMAGE clone numbers 457904 and 356188) suggested that they might contain the start and stop codons, respectively, of the mouse ortholog of MMSC1. Sequencing of these clones revealed that this was indeed the case and confirmed the assignment of the translation start and stop codons in MMSC1.

As previously noted, SEQ ID NO:2 sets forth the nucleotide sequence for MMSC1. However, it has been found that the mRNA for MMSC1 is subject to alternate splicing. On the basis of the sequence for MMSC1, genomic clones have been isolated and are being, analyzed to determine splice junctions and alternate splicing for the mRNA. In addition, the PDZ domains of MMSC1 are analyzed in the yeast two-hybrid assay to identify other proteins which interact with MMSC1 and consequently are involved in the MMAC1 tumor suppressor pathway.

Since MMSC1 is an MMAC1 interacting protein that is involved in tumor suppression activity in the MMAC1 pathway, mutations in the MMSC1 gene which affect the interaction of MMSC1 with MMAC1 or affect the interaction of other proteins with MMAC1 as a result of the scaffolding effect of MMSC1 will interfere with the MMAC1 tumor suppressor pathway and lead to tumorigenesis. Thus, an additional aspect of the present invention is the screening of MMSC1 for such mutations using conventional techniques. Such methods may further comprise the step of amplifying a portion of the MMSC1 gene, and may further include a step of providing a set of polynucleotides which are primers for amplification of said portion of the MMSC1 gene. The method is useful for identifying mutations for use in either diagnosis of cancer or prognosis of cancer. Since such variants can now be detected earlier, i.e., before symptoms appear, and more definitively, better treatment options will be available in those individuals identified as having harmful mutations in MMSC1.

The present invention is directed to the determination that the MMSC1 binds to the C-terminal region of MMAC1 and is involved in a common pathway with MMAC1 which is a known tumor suppressor. Since many of the mutations in MMAC1 are frameshift or nonsense mutations which consequently alter the C-terminus of MMAC 1, MMSC1 can be used to assay for normal or mutated MMAC1 proteins using conventional techniques.

Finally, the present invention is directed to a method for screening drug candidates to identify drugs useful for treating or preventing cancer. Drug screening is performed by expressing mutant MMSC1 and assaying the effect of a drug candidate on the binding of MMSC1 with MMAC1. Similarly, one can test the effect of a drug candidate on the binding of wild-type MMSC1 with a mutant MMSC1. Such assays can be performed in vitro or in vivo, such as in oocytes, mammalian cells or transgenic animals. Other assays may test the ability of a drug, wherein the drug may be, e.g., a peptide, to replace the activity of MMSC1 such that the drug plus MMAC1 will work in concert similar to the normal wild-type interactions of MMSC1 and MMAC1. Again, similar assays may be performed to screen for drugs which replace a mutant MMAC1 and will bind to wild-type MMSC1 to replace the MMAC1 function which is lacking as a result of a mutated MMAC1.

According to the diagnostic and prognostic method of the present invention, alteration of the wild-type MMSC 1 gene is detected. In addition, the method can be performed by detecting the wild-type MMSC1 gene and confirming the lack of a cause of cancer as a result of this locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues and are not inherited in the germline. Germline mutations can be found in any of a body's tissues and are inherited. Point mutational events may occur in regulatory regions, such as in the promoter of the gene, leading to loss or diminution of expression of the mRNA. Point mutations may also abolish proper RNA processing, leading to loss of expression of the MMSC1 gene product, or to a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis, hybridization using nucleic acid modified with gold nanoparticles and PCR-SSCP, as discussed in detail further below. Also useful is the recently developed technique of DNA microchip technology.

The presence of cancer due to a germline mutation at this locus may be ascertained by testing any tissue of a human for mutations of the MMSC1 gene. For example, a person who has inherited a germline MMSC1 mutation, especially one which alters the interaction of MMSC1 with MMAC 1, would be prone to develop cancer. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the MMSC1 gene. Alteration of a wild-type MMSC1 allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of cancer cases. Southern blots displaying hybridizing fragments differing in length from control DNA when probed with sequences near or including the MMSC1 locus indicate a possible mutation. If restriction enzymes which produce very large restriction fragments are used, then pulsed field gel electrophoresis (PFGE) is employed.

Detection of point mutations may be accomplished amplification, e.g., PCR, from genomic or cDNA and sequencing the amplified nucleic acid or by molecular cloning of the MMSC1 allele and sequencing the allele using techniques well known in the art.

There are six well known methods for a more complete, yet still indirect, test for confirming the presence of a susceptibility allele: 1) single stranded conformation analysis (SSCP) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Rano and Kidd, 1989). For allele-specific PCR, primers are used which hybridize at their 3' ends to a particular MMSC1 mutation. If the particular mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligo-nucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type MMSC1 gene coding sequence. The ribo-probe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the MMSC1 gene can also be detected using Southern hybridization, especially if the changes are gross rearrangements, such as deletions and insertions.

DNA sequences of the MMSC1 gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the gene. Hybridization of allele-specific probes with amplified MMSC1 sequences can be performed, for example, on a nylon filter. Hybridization to a particular probe under high stringency hybridization conditions indicates the presence of the same mutation in the tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al. 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Nature Genetics, 1996). Also see Fodor (1997).

The most definitive test for mutations in a candidate locus is to directly compare genomic MMSC1 sequences from patients with those from a control population. Alternatively, one could sequence messenger RNA after amplification, e.g., by PCR, thereby eliminating the necessity of determining the exon structure of the candidate gene.

Mutations from patients falling outside the coding region of MMSC1 can be detected by examining the non-coding regions, such as introns and regulatory sequences near or within the genes. An early indication that mutations in noncoding regions are important may come from Northern blot experiments that reveal messenger RNA molecules of abnormal size or abundance in patients as compared to control individuals.

Alteration of MMSC1 mRNA expression can be detected by any techniques known in the art. These include Northern blot analysis, PCR amplification and RNase protection. Diminished mRNA expression indicates an alteration of the wild-type gene. Alteration of wild-type genes can also be detected by screening for alteration of wild-type MMSC1 protein. For example, monoclonal antibodies immunoreactive with MMSC 1 can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered MMSC1 protein can be used to detect alteration of the wild-type MMSC1 gene. Functional assays, such as protein binding determinations, can be used. In addition, assays can be used which detect MMSC1 biochemical function. Finding a mutant MMSC1 gene product indicates alteration of a wild-type MMSC1 gene. One such binding assay is the binding of MMSC1 with wild-type MMAC1. Conversely, wild-type MMSC1 or the PDZ domain interacting with MMAC1 can be used in a protein binding assay or biochemical function assay to detect normal or mutant MMAC1 proteins, where the mutant proteins are proteins lacking a wild-type C-terminus.

A mutant MMSC1 gene or gene product or a mutant MMAC1 can also be detected in other human body samples, such as serum, stool, urine and sputum. The same techniques discussed above for detection of mutant genes or gene products in tissues can be applied to other body samples. By screening such body samples, a simple early diagnosis can be achieved for cancer resulting from a mutation in the MMSC1 gene.

The primer pairs of the present invention are useful for determination of the nucleotide sequence of a particular MMSC1 allele using PCR. The pairs of single-stranded DNA primers for MMSC1 can be annealed to sequences within or surrounding the MMSC1 gene in order to prime amplifying DNA synthesis of the gene itself. A complete set of these primers allows synthesis of all of the nucleotides of the gene coding sequences, i.e., the exons. The set of primers preferably allows synthesis of both intron and exon sequences. Allele-specific primers can also be used. Such primers anneal only to particular MMSC1 mutant alleles, and thus will only amplify a product in the presence of the mutant allele as a template.

In order to facilitate subsequent cloning of amplified sequences, primers may have restriction enzyme site sequences appended to their 5' ends. Alternatively, primers can also be prepared with 5' phosphoryl groups which will allow for blunt end coloning of amplied sequences. Thus, all nucleotides of the primers are derived from MMSC1 sequence or sequences adjacent to MMSC1, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of MMSC1, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the MMSC1 gene or mRNA using other techniques.

Mutations which interfere with the function of the MMSC1 gene product are involved in the pathogenesis of cancer. Thus, the presence of an altered (or a mutant) MMSC1 gene which produces a protein having a loss of function, or altered function, directly increases the risk of cancer. In order to detect a MMSC1 gene mutation, a biological sample is prepared and analyzed for a difference between the sequence of the allele being analyzed and the sequence of the wild-type allele. Mutant MMSC1 alleles can be initially identified by any of the techniques described above. The mutant alleles are then sequenced to identify the specific mutation of the particular mutant allele. Alternatively, mutant alleles can be initially identified by identifying mutant (altered) proteins, using conventional techniques. The mutant alleles are then sequenced to identify the specific mutation for each allele. The mutations, especially those which lead to an altered function of the protein, are then used for the diagnostic and prognostic methods of the present invention.

The identification of the association between the MMSC1 gene mutations and cancer permits the early presymptomatic screening of individuals to identify those at risk for developing cancer. To identify such individuals, MMSC1 alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal MMSC1 gene or appropriate fragment (coding sequence or genomic sequence) are determined and then compared, or (2) the RNA transcripts of the MMSC1 gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the MMSC1 gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal MMSC1 gene.

Alternatively, polymerase chain reactions (PCRs) are performed with primer pairs for the 5' region or the exons of the MMSC1 gene. PCRs can also be performed with primer pairs based on any sequence of the normal MMSC1 gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common MMSC1 gene variants by amplifying the individual's DNA using suitable primer pairs and analyzing the amplified product, e.g., by dot-blot hybridization using allele-specific oligonucleotide probes.

The second method employs RNase A to assist in the detection of differences between the normal MMSC1 gene and defective genes. This comparison is performed in steps using small (~500 bp) restriction fragments of the MMSC1 gene as the probe. First, the MMSC1 gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the MMSC1 gene fragments are transcribed in vitro using the SP6 transcription system, well known in the art, in the presence of $[\alpha\text{-}^{32}P]GTP$, generating radiolabeled RNA transcripts of both strands of the gene.

Individually, these RNA transcripts are used to form heteroduplexcs with the allelic DNA using conventional techniques. Mismatches that occur in the RNA:DNA heteroduplex, owing to sequence differences between the MMSC1 fragment and the MMSC1 allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the MMSC1 gene and the consequent presence of cancer. These variants can take a number of forms. The most severe forms would be frame shift mutations or large deletions which would cause the gene to code for an abnormal protein or one which would significantly alter protein expression. Less severe disruptive mutations would include small in-frame deletions and non-conservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk for cancer at, or even before, birth. Finally, this invention changes our understanding of the cause and treatment of cancer.

Definitions

The present invention employs the following definitions.

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); Wu et al., 1989a (for LCR), U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the MMSC1 region are preferably complementary to, and hybridize specifically to sequences in the MMSC1 region or in regions that flank a target region therein. MMSC1 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf, 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the MMSC1 polypeptide and fragments thereof or to polynucleotide sequences from the MMSC1 region. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the MMSC1 polypeptide or fragment. Monoclonal antibodies may be made by injecting mice with the protein polypeptides, fusion proteins or fragments thereof. Monoclonal antibodies will be screened by ELISA and tested for specific immunoreactivity with MMSC1 polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate tor the aninmal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g. in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse el al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/ complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. In addition, as disclosed herein, MMAC1 and PDZ binding peptides, as well as several other proteins, bind to or interact with MMSC1. Each of these proteins are also considered binding partners herein.

A "biological sample" refers to a sample of tissue or fluid suspected of containing an analyte polynucleotide or polypeptide from an individual including, but not limited to e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

"Encode". A polynucleotide is said to "encode" a polypeptide if, in its native state or when manipulated by methods well known to those skilled in the art it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"MMSC1 Allele" refers to normal alleles of the MMSC1 locus that interact with MMAC1 as well as alleles of MMSC1 carrying variations that affect the interaction with MMAC1 and that cause cancer.

"MMSC1 Locus", "MMSC1 Gene", "MMSC1 Nucleic Acids" or "MMSC1 Polynucleotide" each refer to polynucleotides, all of which are in the MMSC1 region, that are likely to be expressed in normal tissue, certain alleles of which adversely affect the interaction with MMAC1 and result in cancer. The MMSC1 locus is intended to include coding sequences, intervening sequences and regulatory elements controlling transcription and/or translation. The MMSC1 locus is intended to include all allelic variations of the DNA sequence.

These terms, when applied to a nucleic acid, refer to a nucleic acid which encodes a human MMSC1 polypeptide, fragment, homolog or variant, including, e.g., protein fusions or deletions. The nucleic acids of the present invention will possess a sequence which is either derived from, or substantially similar to a natural MMSC1-encoding gene or one having substantial homology with a natural MMSC1-encoding gene or a portion thereof.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g.,., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the MMSC1 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are provided by this invention. Although the wild-type sequence may be employed, it will often be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g. by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a MMSC1-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook el al., 1989 or Ausubel e al., 1992. Reagents useful in applying such techiques, such as restriction enzymes and the like, are widely known in the art and commercially available from such vendors as New England BioLabs, Boehringer Mannheim, Amersham, Promega, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the MMSC1 locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides.

"MMSC1 protein" or "MMSC1 polypeptide" refers to a protein or polypeptide encoded by the MMSC1 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native MMSC1 sequence, preferably in excess of about 90%, and more preferably at least about 95% homologous. Also included are proteins encoded by DNA which hybridize under high or low stringency conditions, to MMSC1-encoding nucleic acids and closely related polypeptides or proteins retrieved by antisera to the MMSC1 protein(s).

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

"Probes". Polynucleotide polymorphisms associated with MMSC1 alleles which predispose to cancer are detected by hybridization with a polynucleotide probe which forms a stable hybrid with that of the target sequence, under highly stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of a MMSC1 susceptibility allele.

Probes for MMSC1 alleles may be derived from the sequences of the MMSC1 region or its cDNA. The probes may be of any suitable length, which span all or a portion of the MMSC1 region, and which allow specific hybridization to the region. If the target sequence contains a sequence identical to that of the probe, the probes may be short, e.g., in the range of about 8–30 base pairs, since the hybrid will be relatively stable under even highly stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding MMSC1 are preferred as probes. This definition therefore includes probes of sizes 8 nucleotides through 9000 nucleotides. The probes may also be used to determine whether mRNA encoding MMSC1 is present in a cell or tissue.

"Protein modifications or fragments" are provided by the present invention for MMSC1 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitiniation, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}$P, ligands which bind to labeled antiligands (e.g. antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of MMSC1 polypeptides. Immunological activities include both immunogenic function in a target immune system, as well as sharing of immunological epitopes for binding, serving as either a competitor or substitute antigen for an epitope of the MMSC1 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for MMSC1 polypeptides or fragments thereof is described below.

The present invention also provides for fusion polypeptides, comprising MMSC1 polypeptides and fragments. Homologous polypeptides may be fusions between two or more MMSC1 polypeptide sequences or between the sequences of MMSC1 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha matins factor. See Godowski et al., 1988.

Fusion proteins will typically be made by either recombinant nucleic acid methods, as described below, or may be chemically synthesized. Techniques for the synthesis of polypeptides are described, for example, in Merrifield, 1963.

"Protein purification" refers to various methods for the isolation of the MMSC1 polypeptides from other biological material, such as from cells transformed with recombinant nucleic acids encoding MMSC1, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogenieity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A MMSC1 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using, protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nuclcotidc bases.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic 5solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 450° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, and preferably at least about 95% identity.

"Substantially similar function" refers to the function of a modified nucleic acid or a modified protein, with reference to the wild-type MMSC1 nucleic acid or wild-type MMSC1 polypeptide. The modified polypeptide will be substantially homologous to the wild-type MMSC1 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type MMSC1 polypeptide. Alternatively, the similarity of function (activity) of the modified polypeptide may be higher than the activity of the wild-type MMSC1 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type MMSC1 gene function produces the modified protein described above.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measure of homology assigned to various substitutions, deletions and other modifications. Conservative substitutions typically include substitutions within the following groups: glycine, alanine; valine, isoleucine, leucinie; aspartic acid, glutamic acid; asparagine, glutamine; serine, threonine; lysine, arginine; and phenylalanine, tyrosine.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

This polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping, including mapping of human chromosome 1, is provided, e.g., in White and Lalouel, 1988.

Preparation of Recombinant or Chemically Synthesized Nucleic Acids: Vectors, Transformation Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian, plant, insect or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage and Carruthers, 1981 or the triester method according to Matteucci and Caruthers, 1981, and may be performed on commercial, automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example, in Sambrook et al., 1989 or Ausubel et al., 1992.

An appropriate promoter and other necessary vector sequences will be selected so as to be functional in the host, and may include, when appropriate, those naturally associated with the MMSC1 gene. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, Cold Spring Harbor, N.Y. (1 983).

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the MMSC1 nucleic acid or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.), 1979. Examples of commonly used mammalian host cell lines are VERO and HeLa cells, Chinese hamster ovary (CHO) cells, and WI38, BHK, and COS cell lines. An example of a commonly used insect cell line is SF9. However, it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of MMSC1 polypeptide.

The probes and primers based on the MMSC1 gene sequence disclosed herein are used to identify homologous MMSC1 gene sequences and proteins in other species. These gene sequences and proteins are used in the diagnostic/prognostic, therapeutic and drug screening methods described herein for the species from which they have been isolated.

Methods of Use: Drug Screening

This invention is particularly useful for screening compounds by using the MMSC1 polypeptide or binding fragment thereof in any of a variety of drug screening techniques. Since MMSC1 acts as a scaffold that binds to MMAC 1, the phosphatase substrate(s) and the (probably oncogene) tyrosine kinase(s), a valuable drug candidate will be a drug that can prevent binding of either the substrate(s) or the tyrosine kinase(s) to MMSC 1.

The MMSC1 polypeptide or fragment employed in such a test may either be free in solution, affixed to a solid support, or borne on a cell surface. One method of drug screening utilizes eukaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a MMSC1 polypeptide or fragment and the agent being tested, or examine the degree to which the formation of a complex between a MMSC1 polypeptide or fragment and a known ligand, e.g., MMAC1, is aided or interfered with by the agent being tested.

Thus, the present invention provides methods of screening for drugs comprising contacting such an agent with a MMSC1 polypeptide or fragment thereof and assaying (i) for the presence of a complex between the agent and the MMSC1 polypeptide or fragment, or (ii) for the presence of a complex between the MMSC 1 polypeptide or fragment and a ligand, by methods well known in the art. In such competitive binding assays the MMSC1 polypeptide or fragment is typically labeled. Free MMSC1 polypeptide or fragment is separated from that present in a protein:protein complex, and the amount of free (i.e., uncomplexed) label is a measure of the binding of the agent being tested to MMSC1 or its interference with or promotion of MMSC1 :ligand binding, respectively. One may also measure the amount of bound, rather than free, MMAC1. It is also possible to label the ligand rather than the MMSC1 and to measure the amount of ligand binding to MMSC1 in the presence and in the absence of the drug being tested.

Another technique for drug screening provides high throughput screening for compounds having suitable binding affinity to the MMSC1 polypeptides and is described in detail in Geysen, PCT published application WO 84/03564, published on Sep. 13, 1984. Briefly stated, large numbers of different small peptide test compounds are synthesized on a solid substrate, such as plastic pills or some other surface. The peptide test compounds are reacted with MMSC1 polypeptide and washed. Bound MMSC1 polypeptide is then detected by methods well known in the art.

Purified MMSC1 can be coated directly onto plates for use in the aforementioned drug screening techniques. However, non-neutralizing antibodies to the polypeptide can be used to capture antibodies to immobilize the MMSC1 polypeptide on the solid phase.

This invention also contemplates the use of competitive drug screening assays in which neutralizing antibodies capable of specifically binding the MMSC 1 polypeptide compete with a test compound for binding to the MMSC1 polypeptide or fragments thereof. In this manner, the antibodies can be used to detect the presence of any peptide which shares one or more antigenic determinants of the MMSC1 polypeptide.

The above screening methods are not limited to assays employing only MMSC1 but are also applicable to studying MMSC1-protein complexes, e.g., the complex which occurs between MMSC1 and MMAC 1. The effect of drugs on the activity of this complex, especially when either the MMSC1 or the MMSC1 binding protein (e.g., MMAC1) contains a mutation is analyzed.

In accordance with these methods, the following assays are examples of assays which can be used for screening for drug candidates.

A mutant MMSC1 (per se or as part of a fusion protein) is combined with a wild-type protein (per se or as part of a fusion protein) to which wild-type MMSC1 binds. This combining is performed in both the presence of a drug and the absence of the drug, and the amount of binding of the mutant MMSC1 with the wild-type protein is measured. If the amount of the binding is more in the presence of said drug than in the absence of said drug, the drug is a drug candidate for treating cancer resulting from a mutation in MMSC1. This assay is useful where the wild-type protein is a tumor suppressor, such as MMAC1.

A wild-type MMSC1 (per se or as part of a fusion protein) is combined with a wild-type protein (per se or as part of a fusion protein) to which wild-type MMSC1 binds. This combining is performed in both the presence of a drug and the absence of the drug, and the amount of binding of the wild-type MMSC1 with the wild-type protein is measured. If the amount of the binding is more in the presence of said drug than in the absence of said drug, the drug is a drug candidate for treating cancer resulting from a mutation in MMSC1. This assay is useful where the wild-type protein is a tumor suppressor, such as MMAC1.

A mutant MMSC1 (per se or as part of a fusion protein) is combined with a wild-type protein (per se or as part of a fusion protein) to which wild-type MMSC1 binds. This combining is performed in both the presence of a drug and the absence of the drug, and the amount of binding of the mutant MMSC1 with the wild-type protein is measured. If the amount of the binding is less in the presence of said drug than in the absence of said drug, the drug is a drug candidate for treating cancer resulting from a mutation in MMSC1. This assay is useful if the protein is an oncoprotein or a substrate of the oncoprotein.

A wild-type MMSC1 (per se or as part of a fusion protein) is combined with a wild-type protein (per se or as part of a fusion protein) to which wild-type MMSC1 binds. This combining is performed in both the presence of a drug and the absence of the drug, and the amount of binding of the wild-type MMSC1 with the wild-type protein is measured. If the amount of the binding is less in the presence of said drug than in the absence of said drug, the drug is a drug candidate for treating cancer resulting from a mutation in MMSC1 or a cancer resulting from a mutation in MMAC1. This assay is useful if the protein is an oncoprotein or a substrate of the oncoprotein.

A mutant protein, which as a wild-type protein binds to MMSC1 (per se or as part of a fusion protein) is combined with a wild-type MMSC1 (per se or as part of a fusion protein). This combining is performed in both the presence of a drug and the absence of the drug, and the amount of binding of the mutant protein with the wild-type MMSC1 is measured. If the amount of the binding is less in the presence of said drug than in the absence of said drug, the drug is a drug candidate for treating cancer resulting from a mutation in the gene encoding the protein.

The polypeptide of the invention may also be used for screening compounds developed as a result of combinatorial library technology. Combinatorial library technology provides an efficient way of testing a potential vast number of different substances for ability to modulate activity of a polypeptide. Such libraries and their use are known in the art. The use of peptide libraries is preferred. See, for example, WO 97/02048.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993). This system may be used as a coarse screen prior to testing a substance for actual ability to modulate activity of the polypeptide. Alternatively, the screen could be used to screen test substances for binding to a MMSC1 specific binding partner, such as MMAC 1, or to find mimetics of the MMSC1 polypeptide.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment (which may include preventative treatment) of cancer, use of such a substance in the manufacture of a composition for administration, e.g., for treatment of cancer, and a method of making a pharmaceutical composition comprising admixing such a substance with a pharmaceutically acceptable excipient, vehicle or carrier, and optionally other ingredients.

A substance identified using as a modulator of polypeptide function may be peptide or non-peptide in nature. Non-peptide small molecules are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a lead compound. This might be desirable where the active compound is difficult or expensive to synthesize or where it is unsuitable for a particular method of administration, e.g., peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the mino acid residues in the peptide, e.g., by substituting each residue in turn. Alanine scans of peptide are commonly used to refine such peptide motifs. These parts or residues constituting the active region of the compound are known as its pharmacophore.

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Nucleic Acid Diagnosis and Diagnostic Kits

In order to detect the presence of a MMSC1 allele predisposing an individual to cancer, a biological sample such as blood is prepared and analyzed for the presence or absence of susceptibility alleles of MMSC1. In order to detect the presence of cancer or as a prognostic indicator, a biological sample is prepared and analyzed for the presence or absence of mutant alleles of MMSC1. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant MMSC1 sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, if desired, to extract the nucleic acids. The sample nucleic acid may be prepared in various ways to facilitate detection of the target sequence, e.g., denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region for MMSC1. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; U.S. Pat. No. 4,868,105; and in EPO Publication No. 225, 807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes, see Jablonski et al., 1986.

Two-step label amplification methodologies are known in the art. These assays work on the principle that a small ligand (such as digoxigenin, biotin, or the like) is attached to a nucleic acid probe capable of specifically binding MMSC1. Allele specific probes are also contemplated within the scope of this example and exemplary allele specific probes include probes encompassing the predisposing mutations of this disclosure.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting MMSC1. Thus, in one example to detect the presence of MMSC1 in a cell sample, more than one probe complementary to the gene is employed and in particular the number of different probes is alternatively two, three, or five different nucleic acid probe sequences. In another example, to detect the presence of mutations in the MMSC1 gene sequence in a patient, more than one probe complementary to these genes is employed where the cocktail includes probes capable of binding to the allele-specific mutations identified in populations of patients with alterations in MMSC1. In this embodiment, any number of probes can be used, and will preferably include probes corresponding to the major gene mutations identified as predisposing an individual to cancer.

Methods of Use: Peptide Diagnosis and Diagnostic Kits

The presence of cancer can also be detected on the basis of the alteration of wild-type MMSC1 polypeptide. Such alterations can be determined by sequence analysis in accordance with conventional techniques. More preferably, antibodies (polyclonal or monoclonal) are used to detect differences in, or the absence of MMSC1 peptides. Techniques for raising and purifying antibodies are well known in the art and any such techniques may be chosen to achieve the preparations claimed in this invention. In a preferred embodiment of the invention, antibodies will immunoprecipitate MMSC1 proteins from solution as well as react with these proteins on Western or immunoblots of polyacrylamide gels. In another preferred embodiment, antibodies will detect MMSC1 proteins in paraffin or frozen tissue sections, using immunocytochemical techniques.

Preferred embodiments relating to methods for detecting MMSC1 or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

Alternatively, alterations in the MMSC1 sequence can be determined by detecting alterations in the interaction of MMSC1 with MMAC1 or the C-terminus of MMAC1. Wild-type MMAC1 or its C-terminus can be bound to a solid phase and the interaction with MMSC1 assayed by conventional techniques. Analogously, alterations in MMAC1 which affect its interaction with MMSC1 can be detected using wild-type MMSC1 or its PDZ domain which interacts with MMAC1 bound to a solid phase.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., MMSC1 polypeptide) by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., MMSC1 polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved MMSC1 polypeptide activity or stability or which act as inhibitors, agonists, antagonists, etc. of MMSC1 polypeptide activity. By virtue of the availability of cloned MMSC1 sequence, sufficient amounts of the MMSC1 polypeptide may be made available to perform such analytical studies as x-ray crystallography. In addition, the knowledge of the MMSC1 protein sequence provided herein will guide those employing computer modeling techniques in place of, or in addition to x-ray crystallography.

Methods of Use: Gene Therapy

According to the present invention, a method is also provided of supplying wild-type MMSC1 function to a cell which carries a mutant MMSC1 allele. Supplying such a function should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner.

As generally discussed above, the MMSC1 gene or fragment, where applicable, may be employed in gene therapy methods in order to increase the amount of the expression products of such gene in cells. It may also be useful to increase the level of expression of the MMSC1 gene even in those persons in which the mutant gene is expressed at a "normal" level, but the gene product is not fully functional.

Gene therapy would be carried out according to generally accepted methods, for example, as described by Friedman, 1991. Cells from a patient would be first analyzed by the diagnostic methods described above, to ascertain the production of MMSC1 polypeptide in the cells. A virus or plasmid vector (see further details below), containing a copy of the MMSC1 gene linked to expression control elements and capable of replicating inside the cells, is prepared. Suitable vectors are known, such as disclosed in U.S. Pat. No. 5,252,479 and PCT published application WO 93/07282. The vector is then injected into the patient. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adeno-associated virus (Muzyczka, 1992; Ohi et al., 1990), herpesviruses including HSV and EBV (Margolskee, 1992; Johnson et al., 1992; Fink et al., 1992; Breakfield and Geller, 1987; Freese et al., 1990), and retroviruses of avian (Brandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Constantini and Lacy, 1981); membrane fusion-mediated transfer via liposomes (Felgner et al., 1987; Wang and Huang, 1989; Kaneda et al., 1989; Stewart et al., 1992; Nabel et al., 1990; Lim et al., 1992); and direct DNA uptake and receptor-mediated DNA transfer (Wolff et al., 1990; Wu et al., 1991; Zenke et al., 1990; Wu et al., 1989b; Wolff et al., 1991; Wagner et al., 1990; Wagner et al., 1991; Cotten et al., 1990; Curiel et al., 1991a; Curiel et al., 1991b).

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Gene transfer techniques which target DNA directly to brain tissue is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy is as follows: patients who carry a MMSC1 susceptibility allele are treated with a gene delivery vehicle such that some or all of their brain precursor cells receive at least one additional copy of a functional normal MMSC1 allele, respectively. In this step, the treated individuals have reduced risk of cancer to the extent that the effect of the susceptible allele has been countered by the presence of the normal allele.

Methods of Use: Peptide Therapy

Peptides which have MMSC1 activity can be supplied to cells which carry a mutant or missing MMSC1 allele. Protein can be produced by expression of the cDNA sequence in bacteria, for example, using known expression vectors. Alternatively, MMSC1 polypeptide can be extracted from MMSC1-producing mammalian cells. In addition, the techniques of synthetic chemistry can be employed to synthesize MMSC1 protein. Any of such techniques can provide the preparation of the present invention which comprises the MMSC1 protein. The preparation is substantially free of other human proteins. This is most readily accomplished by synthesis in a microorganism or in vitro.

Active MMSC1 molecules can be introduced into cells by microinjection or by use of liposomes, for example. Alternatively, some active molecules may be taken up by cells, actively or by diffusion. Supply of molecules with MMSC1 activity should lead to inhibition of cancer. Other molecules with MMSC1 activity (for example, peptides, drugs or organic compounds) may also be used to effect such an inhibition. Modified polypeptides having substantially similar function are also used for peptide therapy.

Methods of Use: Transformed Hosts

Animals for testing therapeutic agents can be selected after mutagenesis of whole animals or after treatment of germline cells or zygotes. Such treatments include insertion of mutant MMSC1 alleles, usually from a second animal species, as well as insertion of disrupted homologous genes. Alternatively, the endogenous MMSC1 gene of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). After test substances have been administered to the animals, the presence of cancer must be assessed. If the test substance prevents or suppresses the appearance of cancer, then the test substance is a candidate therapeutic agent for treatment of cancer. These animal models provide an extremely important testing vehicle for potential therapeutic products.

Methods of Use: Transgenic/Knockout Animals and Models

In one embodiment of the invention, transgenic animals are produced which contain a functional transgene encoding a functional MMSC1 polypeptide or variants thereof. Transgenic animals expressing MMSC1 transgenes, recombinant cell lines derived from such animals and transgenic embryos may be useful in methods for screening for and identifying agents that induce or repress function of MMSC1. Transgenic animals of the present invention also can be used as models for studying indications such as cancers.

In one embodiment of the invention, a MMSC1 transgene is introduced into a non-human host to produce a transgenic animal expressing a human or murine MMSC1 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous MMSC1 by homologous recombination between the transgene and the endogenous gene; or the endogenous (gene may be eliminated by deletion as in the preparation of "knock-out" animals. Typically, a MMSC1 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress MMSC1 or express a mutant form of the polypeptide. Alternatively, the absence of a MMSC1 in "knock-out" mice permits the study of the effects that loss of MMSC1 protein has on a cell in vivo. Knock-out mice also provide a model for the development of MMSC1-related cancers.

Methods for producing knockout animals are generally described by Shastry (1995, 1998) and Osterrieder and Wolf (1998). The production of conditional knockout animals, in which the gene is active until knocked out at the desired time is generally described by Feil et al. (1996), Gagneten et al. (1997) and Lobe and Nagy (1998). Each of these references is incorporated herein by reference.

As noted above, transgenic animals and cell lines derived from such animals may find use in certain testing experiments. In this regard, transgenic animals and cell lines capable of expressing wild-type or mutant MMSC1 may be exposed to test substances. These test substances can be screened for the ability to enhance wild-type MMSC1 expression and or function or impair the expression or function of mutant MMSC1.

Pharmaceutical Compositions and Routes of Administration

The MMSC1 polypeptides, antibodies, peptides and nucleic acids of the present invention can be formulated in pharmaceutical compositions, which are prepared according to conventional pharmaceutical compounding techniques. See, for example, *Remington's Pharmaceutical Sciences*, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in an therapeutically effective amount. The actual amount administered, and the rate and time-course of administration, will depend on the nature and severity of the condition being treated. Prescription of treatment, e.g. decisions on dosage, timing, etc., is within the responsibility of general practitioners or spealists, and typically takes account of the disorder to be treated, the condition of the individual patient, the site of delivery, the method of administration and other factors known to practitioners. Examples of techniques and protocols can be found in *Remington's Parmaceutical Sciences*.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635. designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

EXAMPLES

The present invention is further detailed in the following Examples, which are offered by way of illustration and are not intended to limit the invention in any manner. Standard techniques well known in the art or the techniques specifically described below are utilized.

Example 1

Identification of MMSC1

A yeast two-hybrid assay was performed using conventional techniques, such as described by Fields and Song (1989), Chevray and Nathans (1992), Bartel et al. (1993) and Lee et al. (1995). Sequence encoding the C-terminal 15 amino acids of MMAC1 (NEPFDEDQHTQITKV; SEQ ID NO:6) plus its stop codon was generated using an oligonucleotide synthesizer and was ligated to plasmid pGBT.C such that the coding sequence of MMAC1 was in-frame with coding sequence for the Gal4p DNA-binding domain. This plasmid construct was introduced into the yeast reporter strain J692 along with a library of activation domain fusion plasmids prepared from human kidney cDNA (Clontech). Transformants were spread onto 20–150 mm plates of yeast minimal media lacking leucine, tryptophan, and histidine, and containing 25 mM 3-amino-1,2,4-triazole (Gietz et al., 1995; Bartel and Fields, 1995). After one week incubation at 30° C., yeast colonies were assayed for expression of the lacZ reporter gene by beta-galactosidase filter assay (Breeden and Naysmyth, 1985). Colonies that both grew in the absence of histidine and were positive for production of beta-galactosidase were chosen for further characterization.

The activation domain plasmid was purified from positive colonies by the smash-and-grab technique. These plasmids were introduced into E. coli DH10B (Gibco BRL) by electroporation and purified from E. coil by the alkaline lysis method. To test for the specificity of the interaction, specific activation domain plasmids were cotransformed into strain J692 with plasmids encoding various DNA-binding domain fusion proteins, including fusions to C-terminal segments of MMAC1 and human lamin C. Transformants from these experiments were assayed for expression of the HIS3 and lacZ reporter genes. Positives that expressed reporter genes with MMAC1 constructs and not with lamin C constructs encode bona fide MMAC1-interacting proteins. These proteins were identified and characterized by sequence analysis of the insert of the appropriate activation domain plasmid.

Two of the clones encoding bona fide MMAC1-interacting proteins were named pdzk5 and pdzk21. A search of GenBank with the sequences of pdzk5 and pdzk21 revealed that they could be assembled with a partial cDNA sequence, AJ001306, to generate the complete coding sequence of pdzk5. dbEST sequences from two mouse cDNA clones (GenBank accession numbers AA30135 and W50755; IMAGE clone numbers 457904 and 356188) suggested that they might contain the start and stop codons, respectively, of the mouse ortholog of pdzk5. Sequencing of these clones revealed that this was indeed the case and confirmed our assignment of the translational start and stop codons. The nucleotide sequence for MMSC1 is set forth in SEQ ID NO:2 with the amino acid sequence of the encoded protein set forth in SEQ ID NO:3.

FIG. 1 shows a diagram of MMSC1 indicating the position of the 11 PDZ domains and the overlap of the two mouse cDNA clones. FIG. 2 shows an alignment of the first 300 nucleotides of human MMSC1 (H.s._MMSC1) with its translation product (H.s._MMSC1.pep) and the corresponding sequence from the mouse ortholog (M.m._MMSC1; SEQ ID NO:4), as determined from an analysis of the sequence from the above noted clones, with its translation product (M.m._MMSC1.pep; SEQ ID NO:5). Gaps have been introduced into the mouse sequence to optimize the alignment. The in-frame stop codon at nucleotide 93, shared by the mouse and human sequences, demonstrates that the start codon at nucleotide 115 has been correctly identified. The 11 PDZ domains correspond to the amino acids of MMSC1 as shown in Table 1.

TABLE 1

Sequence Correspondence of 11 PDZ Domains

| Domain Number | Amino Acid Span |
| --- | --- |
| 1 | 133–219 |
| 2 | 247–326 |
| 3 | 364–451 |
| 4 | 558–637 |
| 5 | 685–771 |
| 6 | 1067–1158 |
| 7 | 1238–1320 |
| 8 | 1436–1518 |
| 9 | 1532–1613 |
| 10 | 1675–1760 |
| 11 | 1798–1882 |

The nucleotide sequence of MMSC1 was compared with the sequence of GenBank accession number AJ001306. Other than sequencing errors, the following major differences were noted. First, the AJ001306 is missing at least one exon and possibly more (nucleotides 4492–4575 of SEQ ID NO:2). The absence of this exon knocks out PDZ domain number 8. Second, the AJ001306 sequence is either alternatively spliced or unspliced at nucleotide 4770 (relative to sEQ ID NO:2) which results in a stop codon at nt 4771 (relative to SEQ ID NO:2). This would knock out PDZ domains 9, 10 and 11.

Example 2

Identification of MMSC1-Interacting Proteins by Two-Hybrid Analysis

DNA fragments encoding all or portions of MMSC1 are ligated to a two-hybrid DNA-binding domain vector such as pGBT.C such that the coding sequence of MMSC1 is in-frame with coding sequence for the Gal4p DNA-binding domain. These DNA fragments may encode specific PDZ domains of MMSC1 plus the 5 to 10 amino acids N- and C-terminal of each specific PDZ. A plasmid that encodes a DNA-binding domain fusion to a fragment of MMSC1 PDZ is introduced into the yeast reporter strain (such as J692) along with a library of cDNAs fused to an activation domain. Transformants are spread onto 20–150 mm plates of selective media, such as yeast minimal media lacking leucine, tryptophan, and histidine, and containing 25 mM 3-amino-1,2,4-triazole. After one week incubation at 30° C., yeast colonies are assayed for expression of the lacZ reporter gene by beta-galactosidase filter assay. Colonies that both grow in the absence of histidine and are positive for production of beta-galactosidase are chosen for further characterization.

The activation domain plasmid is purified from positive colonies by the smash-and-grab technique. These plasmids are introduced into E. Coli (e.g., DH10B (Gibco BRL)) by electroporation and purified from E. coli by the alkaline lysis method. To test for the specificity of the interaction, specific activation domain plasmids are cotransformed into strain J692 with plasmids encoding various DNA-binding domain fusion proteins, including fusions to segments of MMSC1 and human lamin C. Transformants from these experiments are assayed for expression of the HIS3 and lacZ reporter genes. Positives that express reporter genes with MMSC1 constructs and not with lamin C constructs encode bona fide MMSC1-interacting proteins. These proteins are identified and characterized by sequence analysis of the insert of the appropriate activation domain plasmid.

Example 3

Characterization of the Binding Specificity of MMSC1 PDZ Domains by Two-Hybrid Analysis DNA fragments encoding specific PDZ domains of MMSC1 plus the 5 to 10 amino acids N- and C-terminal of each specific PDZ domain are generated by PCR amplification. These fragments are ligated to a two-hybrid DNA-binding domain vector such as pGBT.C such that the coding sequence of MMSC1 is in-frame with coding sequence for the Gal4p DNA-binding domain. An activation domain library is prepared that encodes an activation domain fused in-frame to random peptide sequences that end with a stop codon. An example of this type of library is the Clontech random peptide library. A plasmid that encodes a DNA-binding domain fusion to a specific MMSC1 PDZ domain is introduced into the yeast reporter strain (such as J692) along with a library of random peptides fused to an activation domain. Transformants are spread onto 20–150 mm plates of selective media, such as yeast minimal media lacking leucine, tryptophan, and histidine, and containing 25 mM 3-amino-1,2,4-triazole. After one week incubation at 30° C., yeast colonies are assayed for expression of the lacZ reporter gene by beta-galactosidase filter assay. Colonies that both grow in the absence of histidine and are positive for production of beta-galactosidase are chosen for sequence analysis. The insert of the activation domain construct is characterized by sequence analysis. The sequence of the peptide that binds to the MMSC1 PDZ domain is obtained by conceptual translation of the nucleotide sequence. Peptide sequences from multiple isolates are aligned to determine a consensus binding motif. This motif can be used to identify cellular proteins that bind MMSC1 and to develop small molecules that inhibit binding to these specific PDZ domains.

Example 4

In vitro Protein-Protein Interaction Assay cDNAs encoding each of the MMSC1 PDZ domains (amino acid residues identified in Table 1), and any desired control proteins, were generated by PCR and subcloned as glutathione S-transferase (GST) fusions in pGEX vectors (Pharmacia). After sequencing to confirm expression construct integrity, the resulting clones were expressed in E. coli and the desired fusion proteins isolated with glutathione-agarose and recovered with glutathione elution. These fusion proteins or control proteins were then adsorbed to different wells of a 96-well ELISA plate and remaining sites blocked with BSA. Synthetic commercially synthesized peptides encoding the desired PDZ-binding domain (i.e., the 16 C-terminal amino acids of MMAC1, or the C-terminal peptide sequences of interacting proteins identified by the approach of Example 2, or the C-terminal peptide sequences identified by the approach of Example 3), or a control peptide, and biotinylated at the amino-terminus, were pre-bound to streptavidin-alkaline phosphatase in a 4:1 molar ratio. The biotinylated peptide streptavidin-alkaline phosphatase complexes were then blocked with free biotin. These pre-bound peptide streptavidin-alkaline phosphatase complexes were then incubated with the immobilized PDZ domains in wash buffer containing PBS, BSA and triton-X100. Unbound material was removed with repeated washes. Bound peptide/streptavidin-alkaline phosphatase complex was then quantitated by a colorimetric phosphatase assay read on a 96-well plate reader.

The following peptides were used in the initial study:

SH3 binding peptide biotin-SGSGILAPPVPPRNTR-COOH (SEQ ID NO:7)

AF6 PDZ binding peptide biotin-SGDDGDDPFLQYEFYV-COOH (SEQ ID NO:8)

MMAC1.388–403 biotin-ENEPFDEDQHTQITKV-COOH (SEQ ID NO:9).

The results of the peptide binding ELISA assay is set forth in Table 2.

TABLE 2

| PDZ Binding Assay | | |
|---|---|---|
| MMSc1 PDZ | Peptide | A405 |
| 3 | SH3 | 0.01 |
|  | AF6 | 2.24 |
|  | MMAC | 0.01 |
| 5 | SH3 | 0.00 |
|  | AF6 | 0.02 |
|  | MMAC | 0.00 |
| 6 | SH3 | 0.00 |
|  | AF6 | 1.46 |
|  | MMAC | 0.23 |
| 7 | SH3 | 0.01 |
|  | AF6 | 1.05 |
|  | MMAC | 1.25 |
| 8 | SH3 | 0.00 |
|  | AF6 | 0.29 |
|  | MMAC | 0.30 |
| 9 | SH3 | 0.02 |
|  | AF6 | 2.41 |
|  | MMAC | 0.10 |

The GST-affinity pull down assay is a complementary in vitro method for investigating protein-protein interactions. PDZ domain-GST fusion proteins are incubated with synthetic biotinylated peptides in wash buffer (these peptides were described above). Streptavidin magnetic beads are then added to recover the biotinylated peptide, then unbound material removed by washing. The beads are then incubated with SDS/DTT loading buffer at 100° C. and bound protein detected by SDS/PAGE and coomasie blue staining.

Example 5

Mutation Screening of MMSC1

Nested PCR amplifications were performed on cDNA from tumor cell lines. Total cell line RNAs were reverse transcribed with Superscript II (Life Technologies) and random hexamers. Using the outer primer pair from each amplicon (i.e. PDZK5.1A and PDZK5.1P or PDZK5.2A and PDZK5.2P), approximately 10 ng of cDNA from each cell line was amplified for 26 cycles. Products were diluted 60 fold and then reamplified for 22–26 cycles using nested M13 tailed primers (i.e. PDZK5.1B and PDZK5.1Q or PDZK5.2B and PDZK5.2Q). Typical primary amplification cycling conditions were an initial denaturation at 95° for 60 s, followed by 26 cycles of 96° (12 s), 58° (15 s) and 72° (90 s). Typical secondary amplification cycling conditions were an initial denaturation at 95° for 60 s, followed by 22–26 cycles of 96° (12 s), 58° (15 s) and 72° (40 s). The resulting RT-PCR products were sequenced with dye-primer chemistry on ABI377 sequencers. Sequences were examined for the presence of variants using the program Sequencher.

The primers used are set forth in Table 3. The sequence variants are set forth in Table 4.

TABLE 3

Table of Primers

| Name | Primer Sequence | SEQ ID NO: |
|---|---|---|
| PDZK5.1A | CAGGTGAGGCAGGGCCGACA | 10 |
| PDZK5.1P | CTACAGTAGGCAGGGCAACAGG | 11 |
| PDZK5.1B | GTTTTCCCAGTCACGACGCGGGCTCCCACCTGCTCCTC | 12 |
| PDZK5.1Q | AGGAAACAGCTATGACCATGTGAACACTAACAAACCTTTCC | 13 |
| PDZK5.1C | GTTTTCCCAGTCACGACGTCAACTCAACCATATACCCTCA | 14 |
| PDZK5.1R | AGGAAACAGCTATGACCATGGCTGGACATCCTTCACGAAG | 15 |
| PDZK5.1D | GTTTTCCCAGTCACGACGGCCTTGGATTCAGTGTGGTG | 16 |
| PDZK5.1S | AGGAAACAGCTATGACCATCCCCAACAAACTGTTTCAGGC | 17 |
| PDZK5.1E | GTTTTCCCAGTCACGACGCCAGGGAACCAGTCCACACA | 18 |
| PDZK5.1T | AGGAAACAGCTATGACCATCCTGACTGAATTCCCACAG | 19 |
| PDZK5.2A | TCCTGGAGGATTAGCAGATCGAG | 20 |
| PDZK5.2P | GGTAATCCAAAATGCTGAATCCCA | 21 |
| PDZK5.2B | GTTTTCCCAGTCACGACGAAGATTGGTGGCACAAACGTG | 22 |
| PDZK5.2Q | AGGAAACAGCTATGACCATAGCACTGCCAGGTATTATACTT | 23 |
| PDZK5.2C | GTTTTCCCAGTCACGACGAGAATTGTTGGCTATGTTGGAAC | 24 |
| PDZK5.2R | AGGAAACAGCTATGACCATGCTCCAGTTAGAAAGAGAGCTG | 25 |
| PDZK5.2D | GTTTTCCCAGTCACGACGACATCCTCATCTACTTCTCCA | 26 |
| PDZK5.2S | AGGAAACAGCTATGACCATAACTCAGCATCATCTGCAATC | 27 |
| PDZK5.2E | GTTTTCCCAGTCACGACGGGAAAACCTGTTGGGTCCTG | 28 |
| PDZK5.2T | AGGAAACAGCTATGACCATCGACAGCAAACCAAAGTAAAAGG | 29 |
| PDZK5.3A | GTGGATTCCTTTGATGGGCACC | 30 |
| PDZK5.3P | CTTTGAGCCACAACAGGAAGGTC | 31 |
| PDZK5.3B | GTTTTCCCAGTCACGACGTGAGCTGCTTGAGGTCAATGG | 32 |
| PDZK5.3Q | AGGAAACAGCTATGACCATCTAAAGGGTCCTGGTAATCC | 33 |
| PDZK5.3C | GTTTTCCCAGTCACGACGCCCCTGAAGTCAAGATTGTTG | 34 |
| PDZK5.3R | AGGAAACAGCTATGACCATACAACTTTCTTCTTCATTATCTTCC | 35 |
| PDZK5.3D | GTTTTCCCAGTCACGACGGAAATATTGAAAGCTGTGCC | 36 |
| PDZK5.3S | AGGAAACAGCTATGACCATGTCAGAAATTCATGCATCTCC | 37 |
| PDZK5.3E | GTTTTCCCAGTCACGACGAAAGTCTTTCCATTCCCAACAA | 38 |
| PDZK5.3T | AGGAAACAGCTATGACCATCCATACGGCTGTGCCTCCTG | 39 |
| PDZK5.4A | GAGTTATATCAAGATCCCTCACCAT | 40 |
| PDZK5.4P | CAAATATGCTCATGCGTGATCGG | 41 |
| PDZK5.4B | GTTTTCCCAGTCACGACGTTCACTTTGGTACACAGTGGTTG | 42 |
| PDZK5.4Q | AGGAAACAGCTATGACCATAAATCTTCTTGCTCCCTCCTT | 43 |
| PDZK5.4C | GTTTTCCCAGTCACGACGCCCGAATGATGTCCAAGGTCC | 44 |
| PDZK5.4R | AGGAAACAGCTATGACCATGTCCACCAACAATACTGATCC | 45 |
| PDZK5.4D | GTTTTCCCAGTCACGACGAGCCACTGGGGTCCACCGAG | 46 |
| PDZK5.4S | AGGAAACAGCTATGACCATACTCGTGGAGTGGATGACAAAC | 47 |
| PDZK5.4E | GTTTTCCCAGTCACGACGCAGTTGAGGCCATTAAGAAT | 48 |
| PDZK5.4T | AGGAAACAGCTATGACCATCAAGTTCAATAATGTGCAGTTCT | 49 |
| PDZK5.5A | CGCCAATGAAACTTCCTCCTCCT | 50 |
| PDZK5.5P | TCTCCTGTGAGGCATTTCTCATG | |
| PDZK5.5B | GTTTTCCCAGTCACGACGCCTTTACCGACCAAAAAATCAGA | 52 |
| PDZK5.5Q | AGGAAACAGCTATGACCATCTGATTGACTGCATCCTCG | 53 |
| PDZK5.5C | GTTTTCCCAGTCACGACGCATCTGCCATTATTAAGACTGC | 54 |
| PDZK5.5R | AGGAAACAGCTATGACCATGTGAAGTCTGCATCTGTTGAAT | 55 |
| PDZK5.5D | GTTTTCCCAGTCACGACGTCCAACAAAAGTCTCCTTCAGT | 56 |
| PDZK5.5S | AGGAAACAGCTATGACCATAACCTCTAATATCTGGTCACC | 57 |
| PDZK5.5E | GTTTTCCCAGTCACGACGCTATAGTTATCCATGAAGTCT | 58 |
| PDZK5.5T | AGGAAACAGCTATGACCATCCGCCTTTCACGATGTCAG | 59 |

TABLE 3-continued

Table of Primers

| Name | Primer Sequence | SEQ ID NO: |
|---|---|---|
| PDZK5.6A | GAAGGTGCGGCTGGTGGTGTAT | 60 |
| PDZK5.6P | CTTGCTCTGTCACCCAGGCTG | 61 |
| PDZK5.6B | GTTTTCCCAGTCACGACGGGCCTGAGCATCGTTGGGAA | 62 |
| PDZK5.6Q | AGGAAACAGCTATGACCATAACCAGGTTTTGCAGGCCAGT | 63 |
| PDZK5.6C | GTTTTCCCAGTCACGACGTCAGGGTAGTCAGCAGAGTGC | 64 |
| PDZK5.6R | AGGAAACAGCTATGACCATTACCCACATCCGCGTGAGAC | 65 |

TABLE 4

Sequence Variants

| Cell line | Type | nt variant | aa change | note |
|---|---|---|---|---|
| MDA-MB-231 | breast | G1021A | gly->arg | Heterozygous variant[1]. |
| A172 | glioblastoma | A1199C | glu->ala | Heterozygous variant[2]. |
| A172 | glioblastoma | A1312G | ile->val | Heterozygous polymorphism |
| T98G | glioblastoma | A1312G | ile->val | Heterozygous polymorphism |
| T98G | glioblastoma | A3646G | ser->gly | Heterozygous polymorphism |
| NIH OVCAR-3 | ovarian | A3646G | ser->gly | Heterozygous polymorphism |
| MDA-MB-231 | breast | A3646G | ser->gly | Heterozygous polymorphism |
| NIH OVCAR-3 | ovarian | A3959G | his->arg | Homozygous variant[3]. |
| U-373MG | glioblastoma | G4053A | none | Heterozygous polymorphism |
| U-118MG | glioblastoma | G4053A | none | Heterozygous polymorphism |
| T98G | glioblastoma | G4053A | none | Heterozygous polymorphism |
| MDA-MB-231 | breast | G4053A | none | Homozygous polymorphism[4] |
| U-118MG | glioblastoma | C4192G | leu->val | Heterozygous polymorphism |
| T98G | glioblastoma | C4192G | leu->val | Heterozygous polymorphism |
| NIH OVCAR-3 | ovarian | C4192G | leu->val | Heterozygous polymorphism |
| HS700T | pancreatic | C4192G | leu->val | Heterozygous polymorphism |
| HS700T | pancreatic | A4674G | none | Heterozygous polymorphism |

[1]This non-conservative amino acid substitution in MMSC1 PDZ domain #2 is at a glycine residue found at this position in most of the PDZ domains of MMSC1.
[2]This non-conservative amino acid substitution is located just before MMSC1 PDZ domain #3
[3]This is a semi-conservative amino acid substitution in MMSC1 PDZ domain #7. This particular PDZ domain has a high affinity for the C-terminus of MMAC1. If the amino acid substitution interferes with binding by MMAC1, it could be tumorigenic. That the observed variant appears homozygous raises the possibilities that the variant is either hemizygous and the cell line is LOH on the other allele at this position or that the other allele harbors a nearby splice defect. Both of these possibilities are in accord with the notion that this amino acid substitution is deleterious.
[4]That the observed polymorphism appears homozygous raises the possibilities that the polymorphism is either hemizygous and the cell line is LOH on the other allele at this position or that the other allele harbors a nearby splice defect. Both of these possibilities are in accord with the notion that G1021A variant in this cell line is deleterious.

Example 6

Generation of Polyclonal Antibody Against MMSC1

Segments of MMSC1 coding sequence are expressed as fusion protein in E. coli. The overexpressed protein is purified by gel elution and used to immunize rabbits and mice using a procedure similar to the one described by Harlow and Lane, 1988. This procedure has been shown to generate Abs against various other proteins (for example, see Kraemer et al., 1993).

Briefly, a stretch of MMSC1 coding sequence is cloned as a fusion protein in plasmid PET5A Novagen, Inc., Madison, Wis.). After induction with IPTG, the overexpression of a fusion protein with the expected molecular weight is verified by SDS/PAGE. Fusion protein is purified from the gel by electroelution. Identification of the protein as the MMSC1 fusion product is verified by protein sequencing at the N-terminus. Next, the purified protein is used as immunogen in rabbits. Rabbits are immunized with 100 µg of the protein in complete Freund's adjuvant and boosted twice in 3 week intervals, first with 100 µg of immunogen in incomplete Freund's adjuvant followed by 100 µg of immunogen in PBS. Antibody containing serum is collected two weeks thereafter. This procedure is repeated to generate antibodies against the mutant forms of the MMSC1, gene product. These antibodies, in conjunction with antibodies to wild type MMSC1, are used to detect the presence and the relative level of the mutant forms in various tissues and biological fluids.

Example 7

Generation of Polyclonal Antibody Against MMSC1-MMSC1 Interacting Protein Complex MMSC1 is capable of binding to certain proteins, e.g., MMAC1. A complex of the two proteins is prepared, e.g., by mixing purified preparations of each of the two proteins. If desired, the protein complex can be stabilized by cross-linking the proteins in the complex by methods known to those of skill in the art. The protein complex is used to immunize rabbits and mice using a procedure similar to the one described by Harlow and Lane, 1988. This procedure has been shown to generate Abs against various other proteins (for example, see Kraeamer et al., 1993).

Briefly, the purified protein complex is used as immunogen in rabbits. Rabbits are immunized with 100 µg of the protein in complete Freund's adjuvant and boosted twice in 3 week intervals, first with 100 µg of immunogen in incomplete Freund's adjuvant followed by 100 µg of immunogen in PBS. Antibody containing serum is collected two weeks thereafter.

This procedure is repeated to generate antibodies against forms of the complex which comprise mutant MMSC1 or mutant MMSC1 interacting protein (e.g., mutant MMAC1). These antibodies, in conjunction with antibodies to wild type MMSC1 or MMSC1 interacting protein (e.g., MMAC1), are used to detect the presence and the relative level of the mutant forms in various tissues and biological fluids.

Example 8

Generation of Monoclonal Antibodies Specific for MMSC1

Monoclonal antibodies are generated according to the following protocol. Mice are immunized with immunogen comprising intact MMSC1 or MMSC1 peptides (wild type or mutant) conjugated to keyhole limpet hemocyanin using glutaraldehyde or EDC as is well known.

The immunogen is mixed with an adjuvant. Each mouse receives four injections of 10 to 100 μg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of MMSC1 specific antibodies by ELISA or RIA using wild type or mutant MMSC1 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

Example 9

Generation of Monoclonal Antibodies Specific for MMSC1-MMSC1 Interacting Protein Complex Monoclonal antibodies are generated according to the following protocol. Mice are immunized with immunogen comprising MMSC1-MMSC1 interacting protein complexes (wild type or mutant), such as MMAC1, conjugated to keyhole limpet hemocyanin using glutaraldehyde or EDC as is well known. The complexes may be stabilized by cross-linking.

The immunogen is mixed with an adjuvant. Each mouse receives four injections of 10 to 100 μg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of MMSC1-MMSC1 interacting protein complex specific antibodies by ELISA or RIA using wild type or mutant MMSC1-MMSC1 interacting protein complexes as target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development. Antibodies are tested for binding to MMSC1 alone or to MMSC1 interacting protein alone to determine which are specific for the complex as opposed to binding to the individual proteins.

Example 10

Sandwich Assay for MMSC1

Monoclonal antibody is attached to a solid surface such as a plate, tube, bead or particle. Preferably, the antibody is attached to the well surface of a 96-well ELISA plate. 100 μL sample (e.g., serum, urine, tissue cytosol) containing the MMSC1 peptide/protein (wild-type or mutants) is added to the solid phase antibody. The sample is incubated for 2 hrs at room temperature. Next the sample fluid is decanted, and the solid phase is washed with buffer to remove unbound material. 100 μL of a second monoclonal antibody (to a different determinant on the MMSC1 peptide/protein) is added to the solid phase. This antibody is labeled with a detector molecule (e.g., $^{125}$I, enzyme, fluorophore or a chromophore) and the solid phase with the second antibody is incubated for two hrs at room temperature. The second antibody is decanted and the solid phase is washed with buffer to remove unbound material.

The amount of bound label, which is proportional to the amount of MMSC1 peptide/protein present in the sample, is quantified. Separate assays are performed using monoclonal antibodies which are specific for the wild-type MMSC1 as well as monoclonal antibodies specific for each of the mutations identified in MMSC1.

Example 11

Sandwich Assay for MMAC1 Using MMSC1

MMSC1 or PDZ domain 6 of MMSC1 is attached to a solid surface such as a plate, tube, bead or particle. Preferably, MMSC1 or its PDZ domain is attached to the well surface of a 96-well ELISA plate. 100 μL sample (e.g., serum, urine, tissue cytosol) containing the MMAC1 peptide/protein (wild-type or mutants) is added to the solid phase MMSC1. The sample is incubated for 2 hrs at room temperature. Next the sample fluid is decanted, and the solid phase is washed with buffer to remove unbound material. 100 μL of a monoclonal antibody to MMAC1 is added to the solid phase. The antibody is labeled with a detector molecule (e.g., $^{125}$I, enzyme, fluorophore, or a chromophore) and the solid phase with the antibody is incubated for two hrs at room temperature. The antibody is decanted and the solid phase is washed with buffer to remove unbound material. The amount of bound label, which is proportional to the amount of wild-type MMAC1 present in the sample, is quantified.

Example 12

Drug Screening

The invention is useful in screening for drugs which can overcome mutations in MMSC1 and also mutations in MMAC1. The knowledge that MMSC1 and MMAC1 form a complex is useful in designing such assays. If a mutation is present in either MMSC1 or in MMAC1 which prevents the MMSC1-MMAC1 complex from forming, drugs may be screened which will overcome the mutation and allow the protein complex to form and to be active. Such screening assays can be, e.g., a yeast two hybrid assay which is dependent upon two proteins interacting. In such an assay, the presence of a mutant protein may show no activity or low activity in such an assay, while the presence of a useful drug will result in formation of a proper complex which results in activity in the assay.

A simple binding assay which shows the binding, i.e., formation of a complex, can similarly be used as outlined above. Useful drugs will increase the formation of MMSC1-MMAC1 complexes. Antibodies may also be used to monitor the amount of complex present. Antibodies specific for the complex are especially useful. If the presence of a drug increases the amount of complex present then the drug is a good candidate for treating the cancer which is a result of the mutation in either the MMSC1 or the MMAC1.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Anand, R. (1992). *Techniques for the Analysis of Complex Genomes*, (Academic Press).
Anderson, et al. (1980). Proc. Natl. Acad. Sci. USA 77, 5399–5403.
Ausubel, F. M., et al. (1992). Current Protocols in Molecular Biology, (J. Wiley and Sons, N.Y.)
Bartel, P. L. and Fields, S. (1995). "Analyzing protein-protein interactions using the yeast two hybrid system", Methods in Enzymology 254, 241–263.
Bartel, P. L. et al. (1993). "Using the 2-hybrid system to detect protein-protein interactions." In *Cellular Interactions in Development: A Practical Approach*, Oxford University Press, pp. 153–179.
Beaucage and Carruthers (1981). Tetra. Letts. 22, 1859–1862.
Berkner, et al. (1988). BioTechniques 6, 616–629.
Berkner (1992). Curr. Top. Microbiol. Immunol. 158, 39–61.
Borman, S. (1996). Chemical & Engineering News, December 9 issue, pp. 42–43.
Brandyopadhyay and Temin (1984). Mol. Cell. Biol. 4, 749–754.
Breakfield and Geller (1987). Mol. Neurobiol. 1, 337–371.
Breeden, L., and Naysmyth, K. (1985). Cold Spring Harbor Symp. Quant. Biol. 50:643–650.
Brenman, J. E. et al. (1996). "Interaction of Nitric Oxide synthase with the postsynaptic density protein PSD-95 and α1-syntrophin mediated by PDZ domains. *Cell* 84:757–767.
Brinster, et al. (1981). Cell 27, 223–231.
Brinster, R. L. et al. (1985). Proc. Natl. Acad. Sci. USA 82:4438–4442.
Buchschacher and Panganiban (1992). J. Virol. 66, 2731–2739.
Capecchi, M. R. (1989). Science 244, 1288.
Cariello (1988). Human Genetics 42, 726.
Chee, M., et al. (1996). Science 274, 610–614.
Chevray, P. M. & Nathans, D. N. (1992). "Protein interaction cloning in yeast: identification of mammalian proteins that react with the leucine zipper of jun." *Proc. Natl. Acad. Sci. USA* 89:5789–5793.
Cho, K. O. et al. (1992). "The rat brain postsynaptic density fraction contains a homolog of the Drosophila discs-large tumor suppressor protein." *Neuron* 9:929–942.
Compton, J. (1991). "Nucleic acid sequence-based amplification." Nature 350, 91–92.
Conner, B. J., et al. (1983). Proc. Natl. Acad. Sci. USA 80, 278–282.
Constantini and Lacy (1981). Nature 294, 92–94.
Cotten, M., et al. (1990). *Proc. Natl. Acad. Sci. USA* 87:4033–4037.
Cotton, R. G., et al. (1988). *Proc. Natl. Acad. Sci. USA* 85:4397–4401.
Curiel, et al. (1991a). Hum. Gene Ther. 3, 147–154.
Curiel, et al. (1991b). Proc. Natl. Acad. Sci. USA 88, 8850–8854.
Deutscher, M. (1990). Meth. Enzymology 182 (Academic Press, San Diego, Calif.).
Donehower, L. A., et al. (1992). Nature 356, 215.
Editorial (1996). Nature Genetics 14, 367–370.
Elghanian, R., et al. (1997). Science 277, 1078–1081.
*Enhancers and Eukaryotic Gene Expression*, Cold Spring Harbor Press, Cold Spring Harbor, N.Y. (1983).
Erickson, J., et al. (1990). Science 249, 527–533.
Fahy, E., et al. (1991). "Self-sustained sequence replication (3SR): an isothermal transcription-based amplification system alternative to PCR." PCR Methods Appl. 1, 25–33.
Feil et al., (1996). Proc. Natl. Acad. Sci. USA 93:10887–10890.
Felgner, et al. (1987). Proc. Natl. Acad. Sci. USA 84, 7413–7417.
Fields, S. & Song, O.-K. (1989). "A novel genetic system to detect protein-protein interactions." *Nature* 340:245–246.
Fiers, et al. (1978). Nature 273, 113.
Fink, et al. (1992). Hum. Gene Ther. 3, 11–19.
Finkelstein, J., et al. (1990). Genomics 7, 167–172.
Fodor, S. P. A. (1997). DNA Sequencing. Massively Parallel Genomics. Science 277, 393–395.
Freese, et al. (1990). Biochem. Pharmacol. 40, 2189–2199.
Friedman, T. (1991). In Therapy for Genetic Diseases, T. Friedman, ed., Oxford University Press, pp. 105–121.
Furnari, F. B. et al. (1997). "Growth suppression of glioma cells by PTEN requires a functional phosphatase catalytic domain. *Proc. Natl. Acad. Sci. USA* 94:12479–12484.
Gagneten et al. (1997). *Nucl. Acids Res.* 25:3326–3331.
Gietz, R. D., et al. (1995). "Studies on the transformation of intact yeast cells by the LiAc/SS-DNA/PEG procedure", Yeast 11. 355–360.
Glover, D. (1985). *DNA Cloning*, I and II (Oxford Press).
Goding (1986). *Monoclonal Antibodies: Principles and Practice*, 2d ed. (Academic Press, N.Y.).
Godowski, et al. (1988). Science 241, 812–816.
Gordon, et al. (1980). Proc. Natl. Acad. Sci. USA 77, 7380–7384.
Gorziglia and Kapikian (1992). J. Virol. 66, 4407–4412.
Graham and van der Eb (1973). Virology 52, 456–467.
Grompe, M. (1993). Nature Genetics 5, 111–117.
Grompe, M., et al. (1989) Proc. Natl. Acad. Sci. USA 86, 5855–5892.
Guthrie, G. and Fink, G. R. (1991). *Guide to Yeast Genetics and Molecular Biology* (Academic Press).
Hacia, J. G., et al. (1996). Nature Genetics 14, 441–447.
Harlow and Lane (1988). Antibodies: A Laboratory Manual (Cold Spring Harbor Laboratory, Cold Spring Harbor, N.Y.).
Harrison, S. C. (1996). "Peptide-surface association: the case of PDZ and PTB domains." *Cell* 86:341–343.

Hasty, P., K., et al. (1991). Nature 350, 243.
Helseth, et al. (1990). J. Virol. 64, 2416–2420.
Hodgson, J. (1991). Bio/Technology 9, 19–21.
Huse, et al. (1989). Science 246, 1275–1281.
Innis, et al. (1990). *PCR Protocols: A Guide to Methods and Applications* (Academic Press, San Diego, Calif.).
Jablonski, E., et al. (1986). Nucl. Acids Res. 14, 6115–6128.
Jakoby, W. B. and Pastan, I. H. (eds.) (1979). Cell Culture. Methods in Enzymology, volume 58 (Academic Press, Inc., Harcourt Brace Jovanovich (New York)).
Johnson, et al. (1992). J. Virol. 66, 2952–2965.
Kaneda, et al. (1989). J. Biol. Chem. 264, 12126–12129.
Kanehisa (1984). Nucl. Acids Res. 12, 203–213.
Kavanaugh, W. M. et al. (1995). "PTB domain binding to signaling proteins through a sequence motif containing phophotyrosine." *Science* 268:1177–1179.
Kennedy, M. B. (1995). "Origin of PDZ (DHR, GLGF) domains." *Trends Biochem. Sci.* 20:350.
Kinszler, K. W., et al. (1991). Science 251, 1366–1370.
Kohler, G. and Milstein, C. (1975). Nature 256, 495–497.
Kong, D. et al. (1997). "PTEN1 is frequently mutated in primary enodmetrial carcinomas." *Nature Genetics* 17:143–144.
Kornau, H. C. et al. (1995). "Domain interactions between NMDA receptor subunits and the postsynaptic density protein PSD-95." *Science* 269:1737–1740.
Kraemer, F. B. et al. (1993). J. Lipid Res. 34, 663–672.
Kubo, T., et al. (1988). FEBS Letts. 241, 119.
Landegren, et al. (1988). Science 242, 229.
Lee, J. E. et al. (1995). *Science* 268:836–844.
Lemmon, M. A. et al. (1996). "PH domains: diverse sequences with a common fold recruit signaling molecules to the cell surface." *Cell* 85:621–624.
Li, D. M. & Sun, H. (1997). Cancer Res. 57:2124–2129.
Li, J. et al. (1997). "PTEN, a putative protein tyrosine phosphatase gene mutated in human brain, breast, and prostate Cancer. *Science* 275:1943–1947.
Liaw, D. et al. (1997). "Germline mutations fo the PTEN gene in Cowden disease, an inherited breast and thyroid cancer syndrome." *Nature Genetics* 16:64–67.
Lim, et al. (1992). Circulation 83, 2007–2011.
Lipshutz, R. J., et al. (1995). Biotechniques 19, 442–447.
Lobe and Nagy (1998). *Bioessays* 20:200–208.
Lockhart, D. J., et al. (1996). Nature Biotechnology 14, 1675–1680.
Louis, D. N. & Gusella, J. F. (1995). "A tiger behind many doors: multiple genetic pathways to malignant glioma." *Trends. Genet.* 11:412–415.
Madzak, et al. (1992). J. Gen. Virol. 73, 1533–1536.
Maldonado, E., et al. (1996). "A human RNA polymerase II complex associated with SRB and DNA-repair proteins", Nature 381, 86–89.
Maniatis, T. et al. (1982). *Molecular Cloning: A Laboratory Manual* (Cold Spring Harbor Laboratory, Cold Spring Harbor, N.Y.).
Mann and Baltimore (1985). J. Virol. 54, 401–407.
Margolskee (1992). Curr. Top. Microbiol. Immunol. 158, 67–90.
Marsh, D. J. et al. (1997). *Nature Genetics* 16:333–334.
Martin, R., et al. (1990). BioTechniques 9, 762–768.
Matteucci, M. D. and Caruthers, M. H. (1981). J. Am. Chem. Soc. 103, 3185.
Matthews and Kricka (1988). Anal. Biochem. 169, 1.
Merrifield (1963). J. Am. Chem. Soc. 85, 2149–2156.
Metzger, et al. (1988). Nature 334, 31–36.
Miller (1992). Curr. Top. Microbiol. Immunol. 158, 1–24.
Miller, et al. (1985). Mol. Cell. Biol. 5, 431–437.
Miller, et al. (1988). J. Virol. 62, 4337–4345.
Modrich, P. (1991). Ann. Rev. Genet. 25, 229–253.
Mombaerts, P., et al. (1992). Cell 68, 869.
Moss (1992). Curr. Top. Microbiol. Immunol. 158, 25–38.
Muzyczka (1992). Curr. Top. Microbiol. Immunol. 158, 97–123.
Nabel, et al. (1990). Science 249, 1285–1288.
Nabel (1992). Hum. Gene Ther. 3, 399–410.
Nelen, M. R. et al. (1997). *Hum. Mol. Genet.* 6:1383–1387.
Newton, C. R., et al. (1989). Nucl. Acids Res. 17, 2503–2516.
Nguyen, Q., et al. (1992). *BioTechniques* 13:116–123.
Novack, et al. (1986). *Proc. Natl. Acad. Sci. USA* 83:586.
Ohi, et al. (1990). Gene 89, 279–282.
Olschwang, S. et al. (1998). *Nature Genetics* 18:12–13.
Orita, M., et al. (1989). Detection of polymorphisms of human DNA by gel electrophoresis as single strand conformation polymorphisms. Proc. Natl. Acad. Sci. USA 86, 2766–2770.
Osterrieder and Wolf (1998). *Rev. Sci. Tech.* 17:351–364.
Page, et al. (1990). J. Virol. 64, 5370–5276.
Pawson, T. (1994). "SH2 and SH3 domains in signal transduction." *Adv. Cancer Res.* 64:87–110.
Pawson, T. & Scott, J. D. (1997). "Signaling through scaffold, anchoring and adaptor proteins." *Science* 278:2075–2080.
Pellicer, et al. (1980). Science 209, 1414–1422.
Petropoulos, et al. (1992). J. Virol. 66, 3391–3397.
Philpott, K. L., et al. (1992). Science 256, 1448.
Quantin, et al. (1992). Proc. Natl. Acad. Sci. USA 89, 2581–2584.
Rano and Kidd (1989). Nucl. Acids Res. 17, 8392.
*Remington's Pharmaceutical Sciences,* 18th Ed. (1990, Mack Publishing Co., Easton, Pa.).
Rigby, P. W. J., et al. (1977). J. Mol. Biol. 113, 237–251.
Rosenfeld, et al. (1992). Cell 68, 143–155.
Sambrook, J., et al. (1989). *Molecular Cloning: A laboratory Manual, 2nd Ed.* (Cold Spring Harbor Laboratory, Cold Spring Harbor, N.Y.).
Sande, S., and Privalsky, M. L. (1996). "Identification of TPACs (T3 Receptor-Associating Cofactors), a family of cofactors that associate with, and modulate the activity of, nuclear hormone receptors", Molecular Endocrin. 10, 813–825.
Scharf (1986). Science 233, 1076.
Schlessinger, J. (1994. "SH2/SH3 signaling proteins." *Curr. Opin. Genet. Dev.* 4:25–30.
Scopes, R. (1982). *Protein Purification: Principles and Practice,* (Springer-Verlag, N.Y.).
Shastry et al. (1995). *Experientia* 51:1028–1039.
Shastry et al. (1998). *Mol. Cell. Biochem.* 181:163 –179.
Shaw, G. (1996). "The plackstrin homology domain: an intriguing multifunctional protein module." *Bioessays* 18:35–46.
Sheffield, V. C., et al. (1989). Proc. Natl. Acad. Sci. USA 86, 232–236.
Sheffield, V. C., et al., (1991). Am. J. Hum. Genet. 49, 699–706.
Shenk, T. E., et al. (1975). Biochemical method for mapping mutational alterations in DNA with S1 nuclease; the location of deletions and temperature-sensitive mutations in simian virus 40. Proc. Natl. Acad. Sci. USA 72, 989–993.
Shieh, B. & Zhu, M. (1996). "Regulation of the TRP $Ca^{2+}$ Channel by INAD in Drosophila Photoreceptors." *Neuron* 16:991–998.
Shimada, et al. (1991). J. Clin. Invest. 88, 1043–1047.

Shinkai, Y., et al. (1992). Cell 68, 855.
Shoemaker, D. D., et al. (1996). Nature Genetics 14, 450–456.
Snouwaert, J. N., et al. (1992). Science 257, 1083.
Songyang, Z. et al. (1997). "Recognition of unique carboxyl-terminal motifs by distinct PDZ domains." *Science* 275:73–77.
Sorge, et al. (1984). Mol. Cell. Biol. 4, 1730–1737.
Spargo, C. A., et al. (1996). "Detection of M. tuberculosis DNA using thermophilic strand displacement amplification." Mol. Cell. Probes 10, 247–256.
Steck, P. A. et al. (1997). "Identification of a candidate tumor suppressor gene, MMAC1, at chromosome 10q23.3 that is mutated in multiple advanced tumors." *Nature Genetics* 15:356–362.
Stewart, et al. (1992). Hum. Gene Ther. 3, 267–275.
Stratford-Perricaudet, et al. (1990). Hum. Gene Ther. 1, 241–256.
Tsunoda, S. et al. (1997). "A multivalent PDZ-domain protein assemblies signaling complexes in a G-protein-coupled cascade." *Nature* 388:243–249.
van der Greer, P. & Pawson, T. (1995). "The PTB domain: a new protein module implicated in signal transduction." *Trends Biochem. Sci.* 20:277–280.
Wagner, et al. (1991). Proc. Natl. Acad. Sci. USA 88, 4255–4259.
Wagner, et al. (1990). Proc. Natl. Acad. Sci. USA 87, 3410–3414.
Walker, G. T., et al. (1992). "Strand displacement amplification—an isothermal, in vitro DNA amplification technique." Nucl. Acids Res. 20, 1691–1696.
Wang and Huang (1989). Biochemistry 28, 9508–9514.
Wartell, R. M., et al. (1990). Nucl. Acids Res. 18, 2699–2705.
Wells, J. A. (1991). Methods in Enzymol. 202, 390–411.
Wetmur and Davidson (1968). J. Mol. Biol. 31, 349–370.
White, M. B., et al. (1992). Genomics 12, 301–306.
White and Lalouel (1988). Ann. Rev. Genet. 22, 259–279.
Wilkinson, et al. (1992). Nucleic Acids Res. 20, 2233–2239.
Wolff, et al. (1990). Science 247, 1465–1468.
Wolff, et al. (1991). BioTechniques 11, 474–485.
Woods, D. F. & Bryant, P. J. (1991). "The discs-large tumor suppressor gene of Drosophila encodes a guanylate kinase homolog localized at septate junctions." *Cell* 66:451–464.
Woods, D. F. & Bryant, P. J. (1993). "ZO-1, DlgA and PSD-95/SAP90: homologous proteins in tight, septate and synaptic cell junctions." *Mech. Dev.* 44: 85–89.
Valancius, V. and Smithies, O. (1991). Mol. Cell Biol. 11, 1402.
Wu, et al. (1989a). Genomics 4:560–569.
Wu, et al. (1989b). J. Biol. Chem. 264, 16985–16987.
Wu, et al. (1991). J. Biol. Chem. 266, 14338–14342.
Zenke, et al. (1990). Proc. Natl. Acad. Sci. USA 87, 3655–3659.

Patents and Patent Applications

European Patent Application Publication No. 0332435.
European Patent Application Publication No. 225,807.
European Patent Application Publication No. 425,731.
Geysen, H., PCT published application WO 84/03564, published 13 Sep. 1984
Hitzeman et al., EP 73,675A.
PCT published application WO 90/07936.
PCT published application WO 92/19195.
PCT published application WO 93/07282.
PCT published application WO 94/25503.
PCT published application WO 95/01203.
PCT published application WO 95/05452.
PCT published application WO 96/02286.
PCT published application WO 96/02646.
PCT published application WO 96/11698.
PCT published application WO 96/40871.
PCT published application WO 96/40959.
PCT published application WO 97/02048.
PCT published application WO 97/12635.
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,376,110.
U.S. Pat. No. 4,486,530.
U.S. Pat. No. 4,683,195
U.S. Pat. No. 4,683,202
U.S. Pat. No. 4,816,567
U.S. Pat. No. 4,868,105.
U.S. Pat. No. 5,252,479.
U.S. Pat. No. 5,270,184.
U.S. Pat. No. 5,409,818.
U.S. Pat. No. 5,455,166.
U.S. Pat. No. 5,550,050

What is claimed is:

1. A synthetic nucleic acid encoding a MMSC1 polypeptide, wherein said polypeptide has the amino acid sequence set forth in SEQ ID NO: 3.

2. The full complementary strand of the synthetic nucleic acid of claim 1.

3. The synthetic nucleic acid of claim 1, wherein said synthetic nucleic acid has the nucleotide sequence set forth in SEQ ID NO: 2.

4. The full complementary strand of the synthetic nucleic acid of claim 3.

5. A vector comprising the synthetic nucleic acid of claim 1.

6. A DNA construct comprising the synthetic nucleic acid of claim 1 operably linked to transcription and translation initiation regulatory sequences.

7. An expression vector comprising the synthetic nucleic acid of claim 1, wherein the synthetic nucleic acid is operably linked to suitable control sequences capable of directing expression of said synthetic nucleic acid in a host cell.

8. A host cell transformed with the expression vector of claim 7.

9. A method of producing a MMSC1 polypeptide wherein the MMS1 polypeptide has the amino acid sequence of SEQ ID NO: 3, wherein said method comprises:

(i) culturing the host cell of claim 8 under conditions suitable for the production of said MMSC1 polypeptide; and (ii) recovering said MMSC1 polypeptide.

10. The method of claim 9, wherein said method further comprises labeling the recovered polypeptide.

11. A vector comprising the synthetic nucleic acid of claim 3.

12. A DNA construct comprising the synthetic nucleic acid of claim 3 operably linked to transcription and translation initiation regulatory sequences.

13. An expression vector comprising the synthetic nucleic acid of claim 3, wherein the synthetic nucleic acid is operably linked to suitable control sequences capable of directing expression of said synthetic nucleic acid in a host cell.

14. A host cell transformed with the expression vector of claim 13.

15. A method of producing a MMSC1 polypeptide wherein the MMS1 polypeptide has the amino acid sequence of SEQ ID NO: 3, wherein said method comprises:

(i) culturing the host cell of claim 14 under conditions suitable for the production of said MMSC1 polypeptide; and (ii) recovering said MMSC1 polypeptide.

16. The method of claim 15, wherein said method further comprises labeling the recovered polypeptide.

* * * * *